United States Patent [19]
Lehrer et al.

[11] Patent Number: 6,040,293
[45] Date of Patent: Mar. 21, 2000

[54] CLAVANINS

[75] Inventors: Robert I. Lehrer, Santa Monica; Chengquan Zhao, Los Angeles, both of Calif.; In-Hee Lee, Seoul, Rep. of Korea

[73] Assignee: The Regents of the University of California, Los Angeles, Calif.

[21] Appl. No.: 08/810,324

[22] Filed: Feb. 28, 1997

Related U.S. Application Data

[63] Continuation-in-part of application No. 08/746,160, Nov. 6, 1996.

[51] Int. Cl.[7] ............................ C07K 14/00; A61K 37/02
[52] U.S. Cl. .............................................. 514/13; 530/326
[58] Field of Search ..................... 514/13, 21; 530/326, 530/323, 332

[56] References Cited

FOREIGN PATENT DOCUMENTS

| | | |
|---|---|---|
| 0 403 458 | 12/1990 | European Pat. Off. . |
| 0 472 987 | 3/1992 | European Pat. Off. . |
| 93 11783 | 6/1993 | WIPO . |

OTHER PUBLICATIONS

Cornelissen, B. J. C. et al., "Strategies for Control of Fungal Diseases with Transgenic Plants," *Plant Physiol* 101:709–712 (1993).

Bensch, K. W. et al., "hBD–1: a novel β–defensin from human plasma," *Febs Lett* 368:331 (1995).

Christensen, B. et al., "Channel–forming properties of cecropins and related model compounds incorporated into planar lipid membranes," *Proc Natl Acad Sci USA* 85:5072 (1988).

Diamond, G. et al., "Tracheal antimicrobial peptide, a cysteine–rich peptide from mammalian tracheal mucosa: Peptide isolation and cloning of a cDNA," *Proc Natl Acad Sci USA* 88:3952 (1991).

Duclohier, H. et al., "Antimicrobial peptide magainin I from Xenopus skin forms anion–permeable channels in planar lipid bilayers," *Biophys J* 56:1017 (1989).

Harwig, S. S. L. et al., "Gallinacins: cysteine–rich antimicrobial peptides of chicken leukocytes," *Febs Lett* 342:281 (1994).

Jones, D. E. et al., "Paneth Cells of the Human Small Intestine Express and Antimicrobial Peptide Gene," *J Biol Chem* 267:23216 (1992).

Kokryakov, V. N. et al., "Protegrins: leukocyte antimicrobial peptides that combine features of corticostatic defensins and tachyplesins," *Febs Lett* 231 (1993).

Lehrer, R. I. et al., "Defensins: Antimicrobial and Cytotoxic Peptides of Mammalian Cells," *Ann Rev Immunol* 11:105 (1992).

Nakamura, T. et al., "Tachyplesin, a Class of Antimicrobial Peptide from the Hemocytes of the Horseshoe Crab (*Tachypleus tridentatus*)," *J Biol Chem* 263:16709–16713 (1988).

Patterson–Delafield, J. et al., "Microbial Cationic Proteins in Rabbit Alveolar Macrophages: a Potential Host Defense Mechanism," *Infect Immun* 30:180 (1980).

Schonwetter, B. S. et al., "Epithelial Antibiotics Induced at Sites of Inflammation," *Science* 267:1645 (1995).

Selsted, M. E. et al., "Purification, Primary Structures, and Antibacterial Activities of β–Defensins, a New Family of Antimicrobia Peptides from Bovine Neutrophils," *J. Biol Chem* 268:6641.

Terry, A. S. et al., "The cDNA Sequence Coding for Pre–pro–PGS (Prepro–magainins) and Aspects of the Processing of This Prepro–polypeptide," *J Biol Chem* 263:5745 (1988).

Zasloff, M. et al., "Antimicrobial activity of synthetic magainin peptides and several analogues," *Proc Natl Acad Sci USA* 85:910 (1988).

Zasloff, M., "Magainins, a class of antimicrobial peptides from Xenopus skin: Isolation, characterization of two active forms, and partial cDNA sequence of a precursor," *Proc Natl Acad Sci USA* 84:5449 (1987).

*Primary Examiner*—Karen Cochrane Carlson
*Attorney, Agent, or Firm*—Morrison & Foerster LLP

[57] ABSTRACT

Novel microbial peptides called clavanins are of the formula

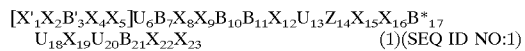

including the salts, esters, amides and acylated forms thereof wherein X is a hydrophobic amino acid residue or modified form thereof;

X' is a small or a hydrophobic amino acid residue or a modified form thereof;

B is a basic amino acid residue or modified form thereof;

B' is basic or a polar/large amino acid residue or modified form thereof; and

B* is a basic or a hydrophobic amino acid residue or a modified form thereof;

U is a small amino acid residue or modified form thereof;

Z is a polar/large amino acid residue or modified form thereof, and wherein 1–5 amino acids is deleted from the N-terminus.

16 Claims, 27 Drawing Sheets

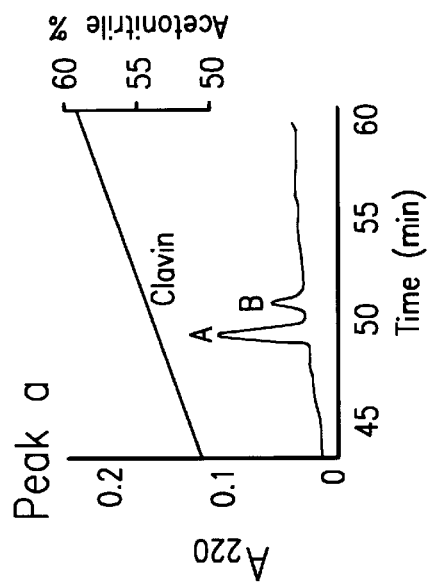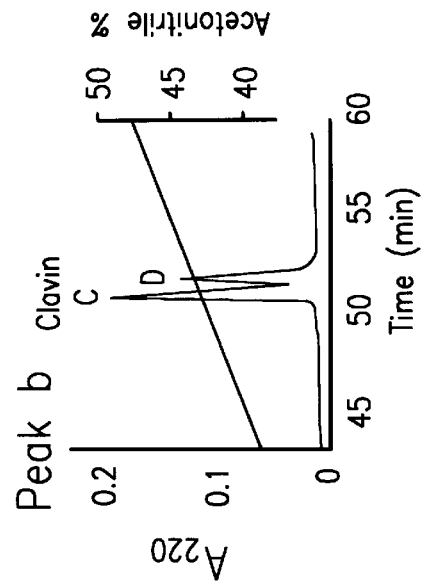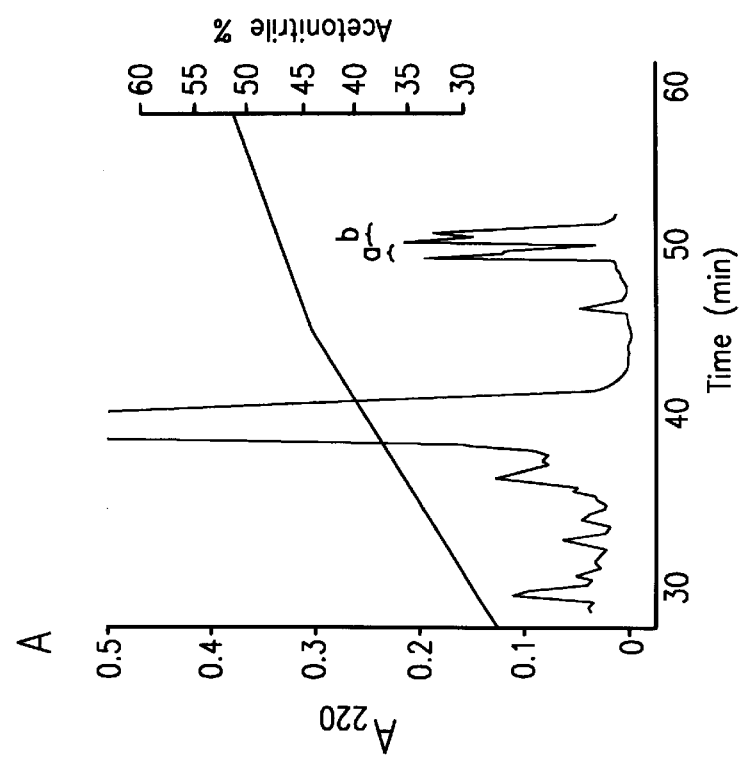

FIG. 3A

The cDNA sequence of Clavanin A

```
  1  ACAAACAACAGGAAAGATGAAAACAACAATTTTGATTCTTCTCATACTGGGACTTGGCAT
                    M  K  T  T  I  L  I  L  L  I  L  G  L  G  I
 61  CAATGCAAAATCTCTGGAGGAAAGAAAATCGGAGGAAGAGAAAGTATTCCAATTCCTTGG
      N  A  K  S  L  E  E  R  K  S  E  E  E  K  V  F  Q  F  L  G
121  CAAAATTATTCATCATGTTGGCAATTTTGTACATGGTTTTAGCCACGTGTTCGGCGACGA
      K  I  I  H  H  V  G  N  F  V  H  G  F  S  H  V  F  G  D  D
181  CCAACAAGATAATGGAAAGTTTTATGGCCACTACGCAGAAGACAATGGCAAGCATTGGTA
      Q  Q  D  N  G  K  F  Y  G  H  Y  A  E  D  N  G  K  H  W  Y
241  TGATACCGGGGATCAATAAAAAAGTTTTAAACAGCTACGCGACTTGAAGACGGACGGACC
      D  T  G  D  Q  ***
301  CGGCAGAACATTGATATTTCTTGTTTTCTTTGATTAAAGGCTAGCCTTATTACTCAGAAT
```

FIG. 3B

The cDNA sequence of Clavanin C

```
  1  CAAACTCAGACAAACAACAGGAAAGATGAAAACAACAATTTTGATTCTTCTCATACTGGG
                             M K T T I L I L L I L G
 61  ACTTGGCATCAATGCAAAATCTCTGGAGGAAAGAAAATCGGAGGAAGAAAAAGTATTCCA
     L G I N A K S L E E R K S E E E K V F H
121  TCTCCTTGGCAAAATTATTCATCATGTTGGCAATTTTGTATATGGTTTTAGCCACGTGTT
     L L G K I I H H V G N F V Y G F S H V F
181  CGGCGACGACCAACAAGATAATGGAAAGTTTTATGGCCACTACGCAGAAGACAATGGCAA
       G D D Q Q D N G K F Y G H Y A E D N G K
241  GCATTGGTATGATACCGGGGATCAATAAAAAAGTTTTAAACAGCTACGCGACTTGAAGAC
     H W Y D T G D Q ***
301  GGACGGACCCGGCAGAACATTGATATTTCTTGTTTTCTTTGATTAAAGGCTAGCCTTATT

361  ACTCAGAATATAACACTACATTGCATTC
```

FIG. 3C

The cDNA sequence of Clavanin D

```
  1  CAGACAAACAACAGGAAAGATGAAAACAACAATTTTGATTCTTCTCATACTGGGACTTGG
                       M  K  T  T  I  L  I  L  L  I  L  G  L  G
 61  CATCAATGCAAAATCTCTGGAGGAAAGAAAATCGGAGGAAGAGAAAGCTTTCAAACTCCT
      I  N  A  K  S  L  E  E  R  K  S  E  E  E  K  A  F  K  L  L
121  TGGCAGAATTATTCATCATGTTGGCAATTTTGTATATGGTTTTAGCCACGTGTTCGGCGA
      G  R  I  I  H  H  V  G  N  F  V  Y  G  F  S  H  V  F  G  D
181  CGACCAACAAGATAATGGAAAGTTTTATGGCCACTACGCAGAAGACAATGGCAAGCATTG
      D  Q  Q  D  N  G  K  F  Y  G  H  Y  A  E  D  N  G  K  H  W
241  GTATGATACCGGGGATCAATAAAAAAGTTTTAAACAGCTACGCGACTTGAAGACGGACGG
      Y  D  T  G  D  Q ***
301  ACCCGGCAGAACATTGATATTTCTTGTTTTCTTTGATTAAAGGCTAGCCTTATTAC
```

FIG. 3D

The cDNA sequence of Clavanin E

```
  1  CAAACTCAGACAAACAACAGGAAAGATGAAAACAACAATTTTGATTCTTCTCATACTGGG
                              M  K  T  T  I  L  I  L  L  I  L  G
 61  ACTTGGCATCAATGCAAAATCTCTGGAGGAAAGAAAATCGGAGGAAGAGAAATTATTCAA
      L  G  I  N  A  K  S  L  E  E  R  K  S  E  E  E  K  L  F  K
121  ACTCCTTGGCAAAATTATTCATCATGTTGGCAATTTTGTACATGGTTTTAGCCACGTGTT
      L  L  G  K  I  I  H  H  V  G  N  F  V  H  G  F  S  H  V  F
181  CGGCGACGACCAACAAGATAATGGAAAGTTTTATGGCTACTACGCAGAAGACAATGGCAA
      G  D  D  Q  Q  D  N  G  K  F  Y  G  Y  Y  A  E  D  N  G  K
241  GCATTGGTATGATACCGGGGATCAATAAAAAAGTTTTAAACAGCTACGCGACTTGAAGAC
      H  W  Y  D  T  G  D  Q  ***
301  GGACGGACCC GG
```

FIG. 3E

SIGNAL SEQUENCE AND ANIONIC PROPIECE

```
CLAV_A   MKTTILILLILGLGINAKSLEERKSEEEK
         ||||||||||||||||||||||||||||
CLAV_C   MKTTILILLILGLGINAKSLEERKSEEEK
         ||||||||||||||||||||||||||||
CLAV_D   MKTTILILLILGLGINAKSLEERKSEEEK
         ||||||||||||||||||||||||||||
CLAV_E   MKTTILILLILGLGINAKSLEERKSEEEK
```

MATURE PEPTIDE AND ANIONIC POSTPIECE

```
CLAV_A   VFQFLGKIIHHVGNFVHGFSHVFGDDQQDNGKFYGHYAEDNGKHWYDTGDQ
         |··||||||||||||·||||||||||||||||||||||||||||||||||
CLAV_C   VFHLLGKIIHHVGNFVYGFSHVFGDDQQDNGKFYGHYAEDNGKHWYDTGDQ
         ·|·||||||||||||||||||||||||||||||·||||||||||||||||
CLAV_D   AFKLLGRIIHHVGNFVYGFSHVFGDDQQDNGKFYGHYAEDNGKHWYDTGDQ
         ·||||||||||||||·|||||||||||||||||·||||||||||||||||
CLAV_E   LFKLLGKIIHHVGNFVHGFSHVFGDDQQDNGKFYGYYAEDNGKHWYDTGDQ
```

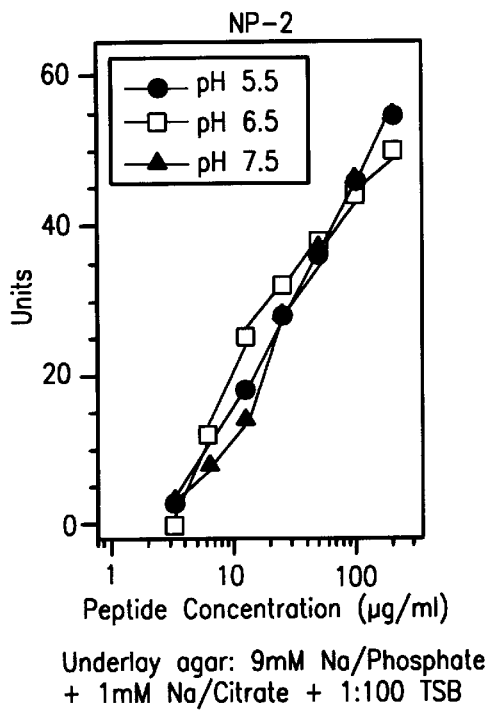

FIG. 6A
The Effect of pH on Antimicrobial Activity Against L. monocytogenes
NP-2
Underlay agar: 9mM Na/Phosphate + 1mM Na/Citrate + 1:100 TSB

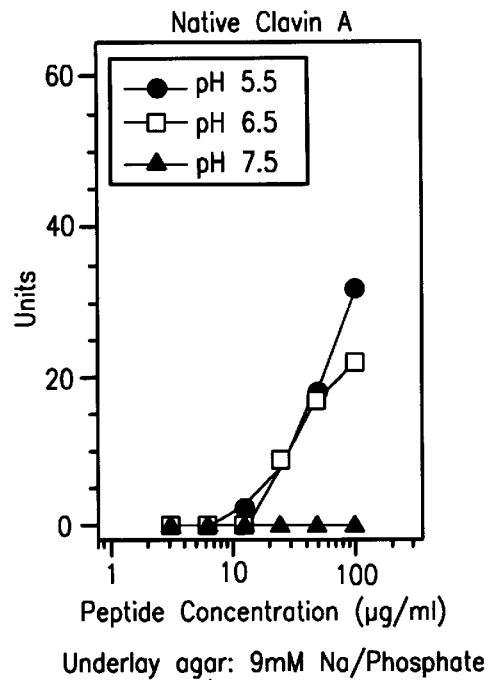

FIG. 6B
The Effect of pH on Antimicrobial Activity Against L. monocytogenes
Native Clavin A
Underlay agar: 9mM Na/Phosphate + 1mM Na/Citrate + 1:100 TSB

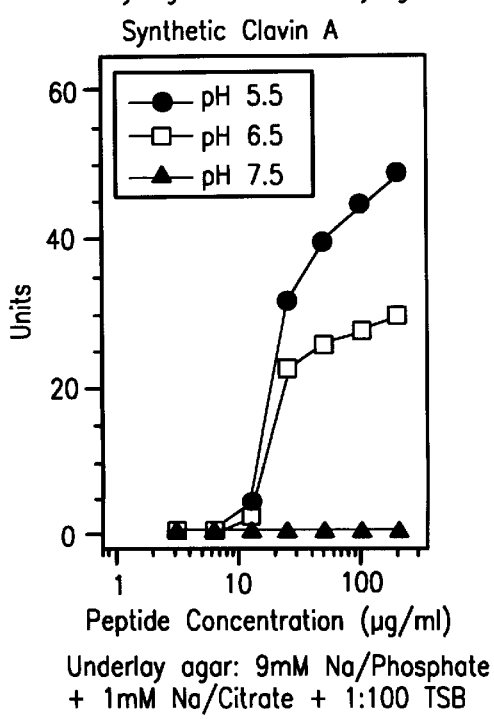

FIG. 6C
The Effect of pH on Antimicrobial Activity Against L. monocytogenes
Synthetic Clavin A
Underlay agar: 9mM Na/Phosphate + 1mM Na/Citrate + 1:100 TSB

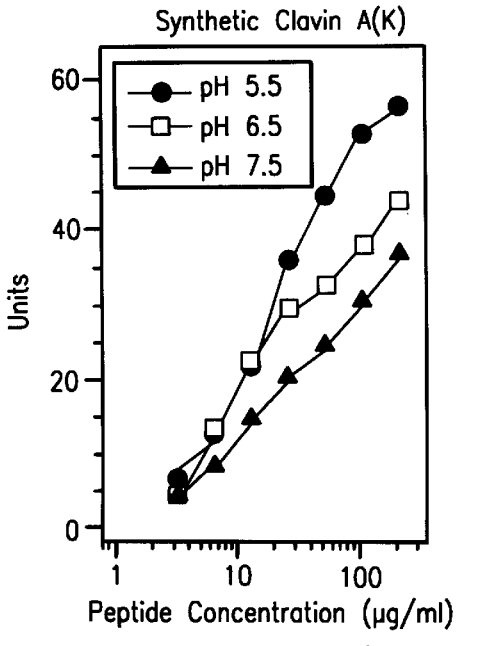

FIG. 6D
The Effect of pH on Antimicrobial Activity Against L. monocytogenes
Synthetic Clavin A(K)
Underlay agar: 9mM Na/Phosphate + 1mM Na/Citrate + 1:100 TSB

FIG. 7A
The Effect of pH on Antimicrobial Activity Against E. coli

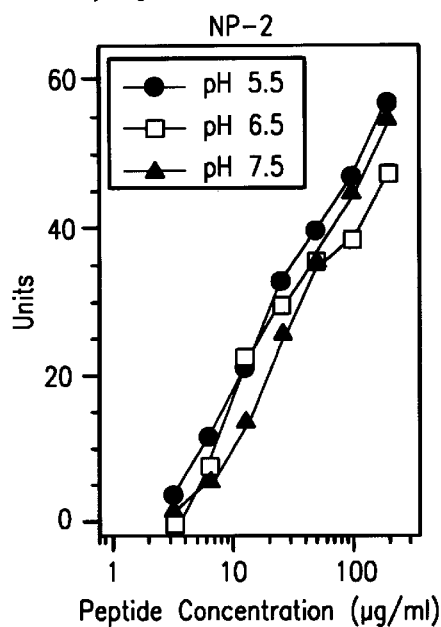

Underlay agar: 9mM Na/Phosphate + 1mM Na/Citrate + 1:100 TSB

FIG. 7B
The Effect of pH on Antimicrobial Activity Against E. coli

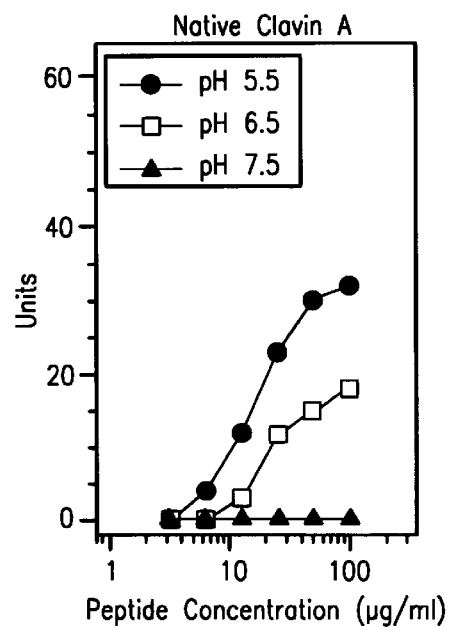

Underlay agar: 9mM Na/Phosphate + 1mM Na/Citrate + 1:100 TSB

FIG. 7C
The Effect of pH on Antimicrobial Activity Against E. coli

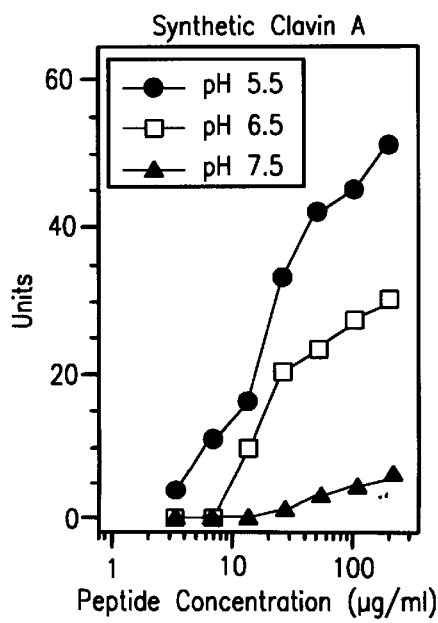

Underlay agar: 9mM Na/Phosphate + 1mM Na/Citrate + 1:100 TSB

FIG. 7D
The Effect of pH on Antimicrobial Activity Against E. coli

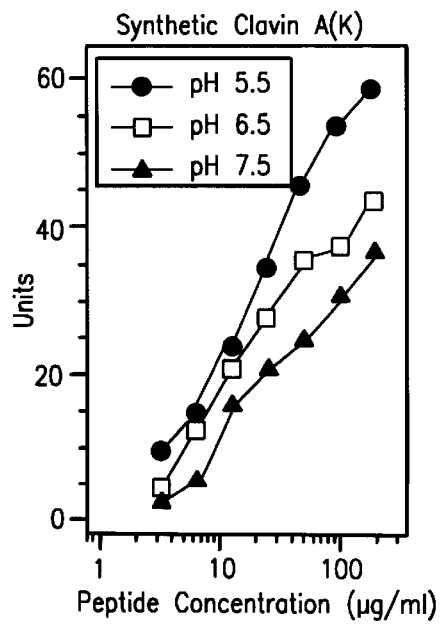

Underlay agar: 9mM Na/Phosphate + 1mM Na/Citrate + 1:100 TSB

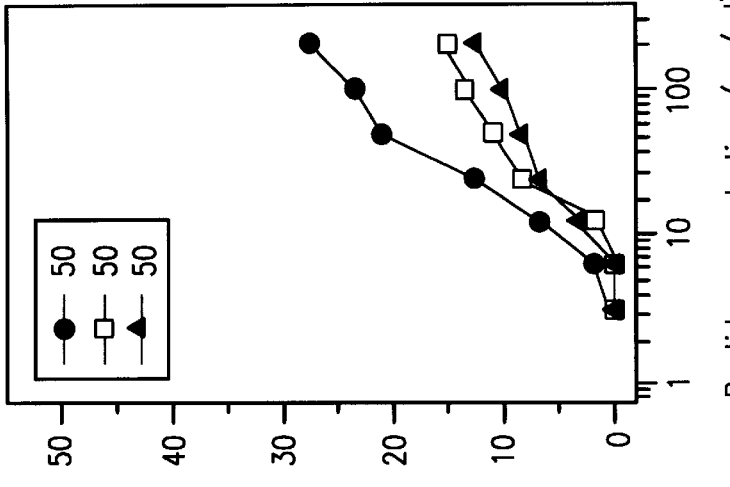
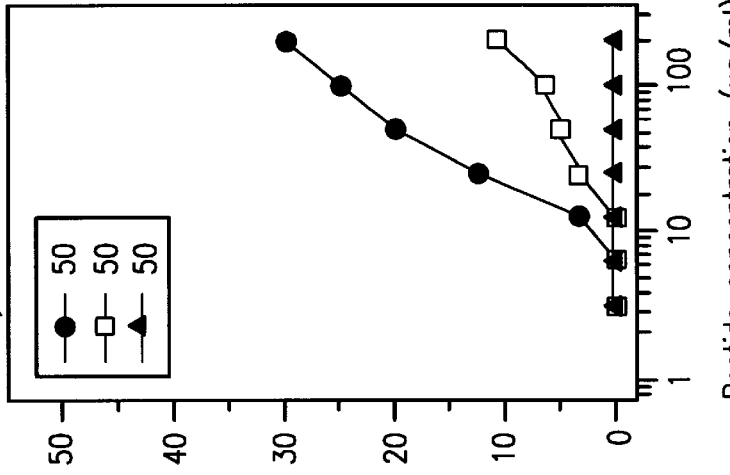
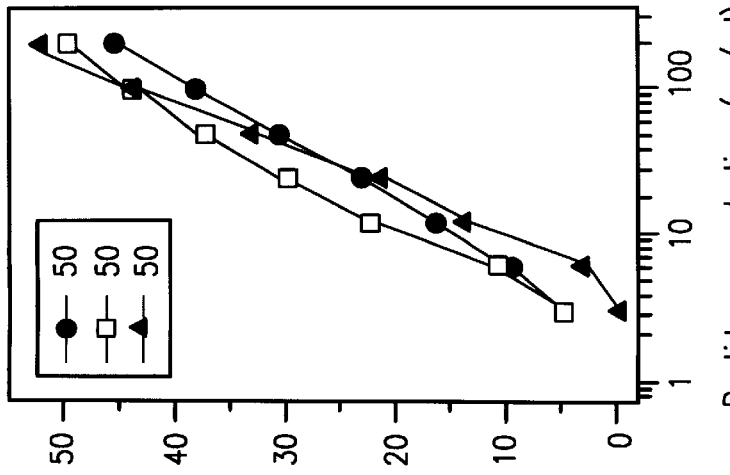

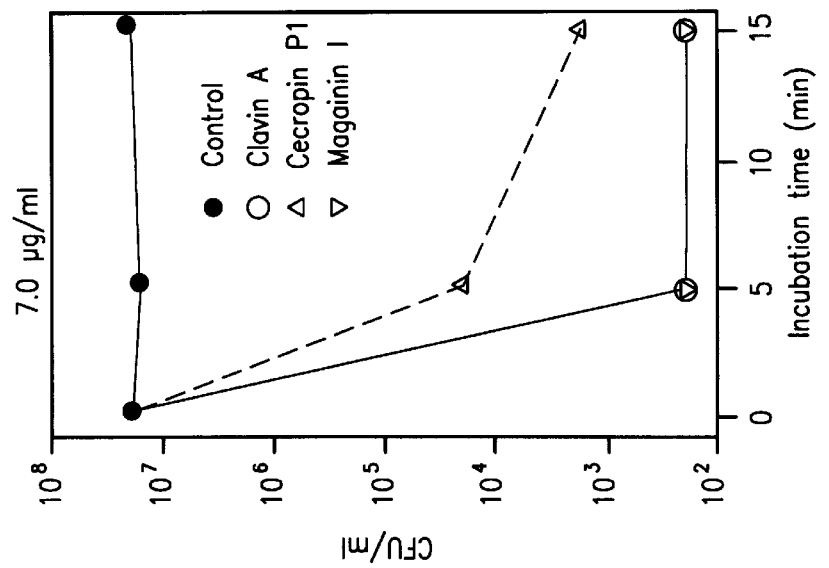
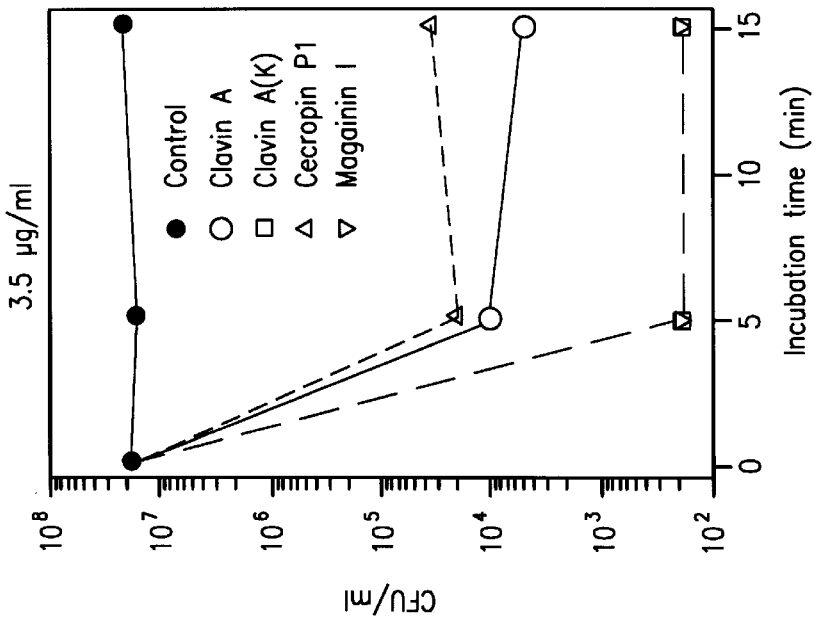

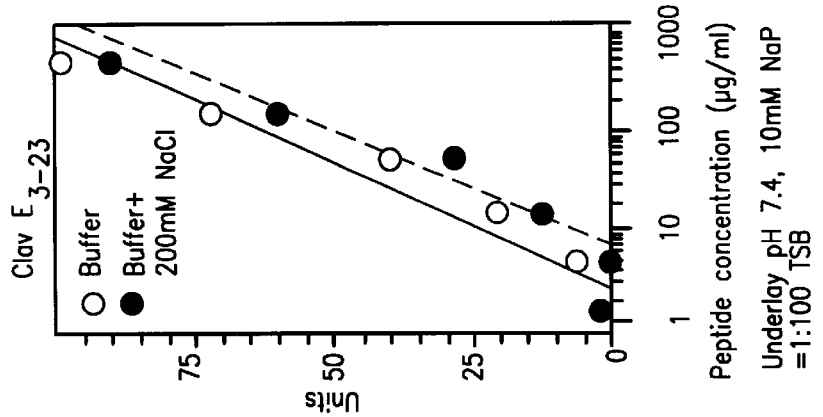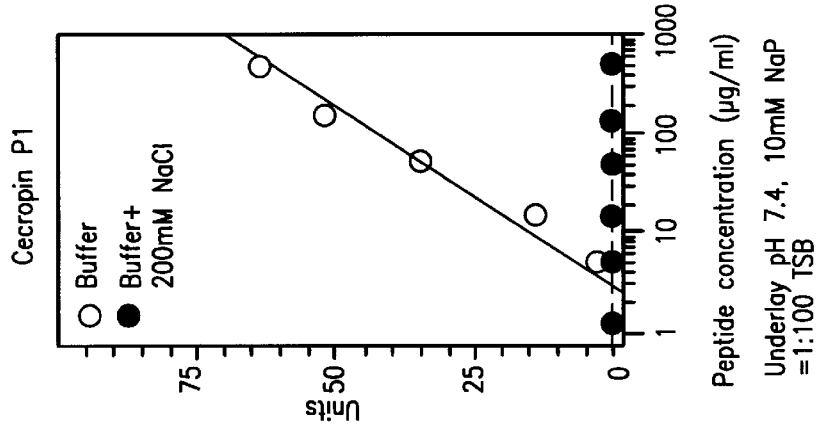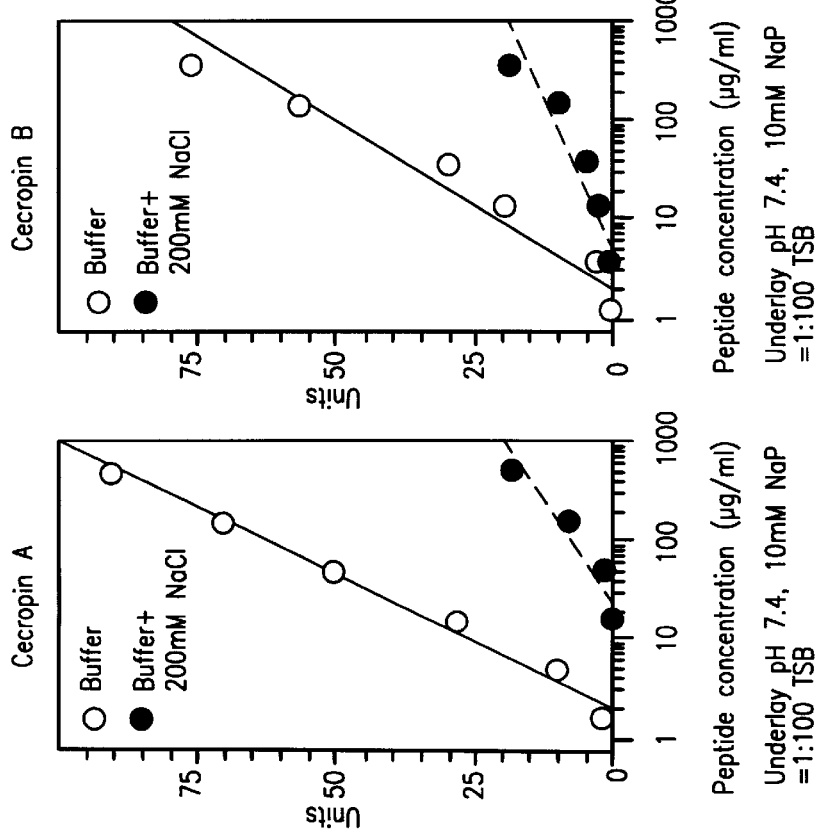

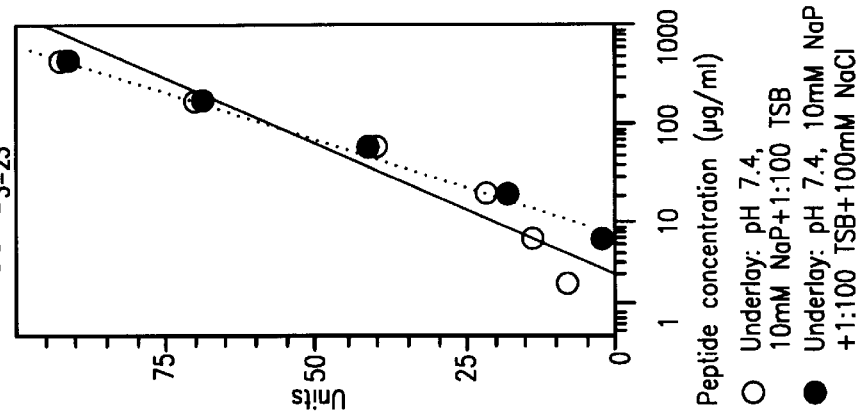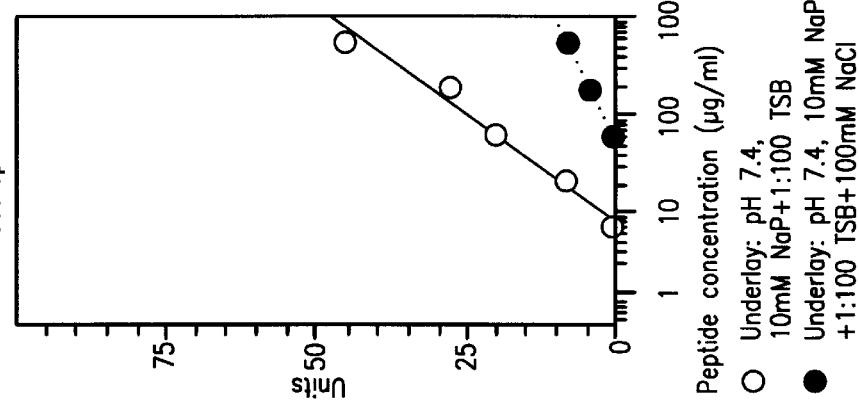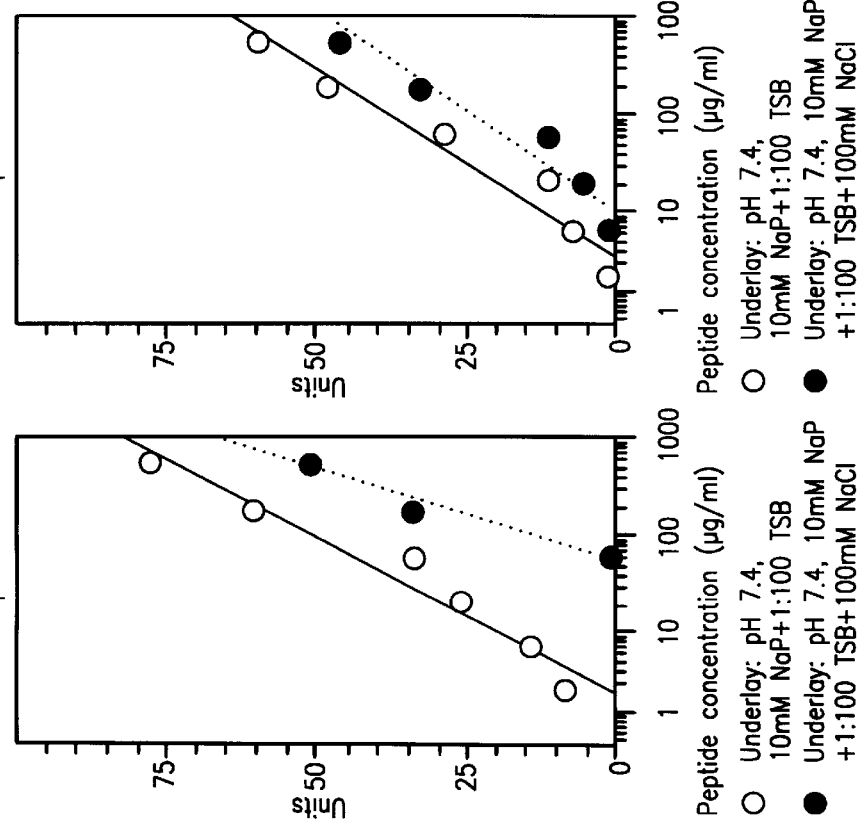

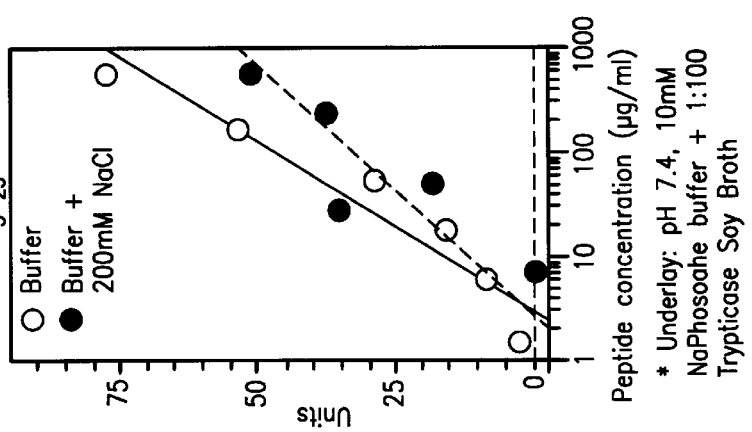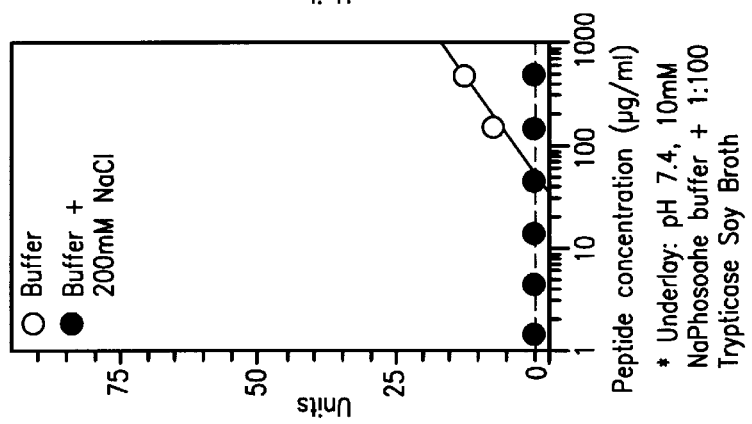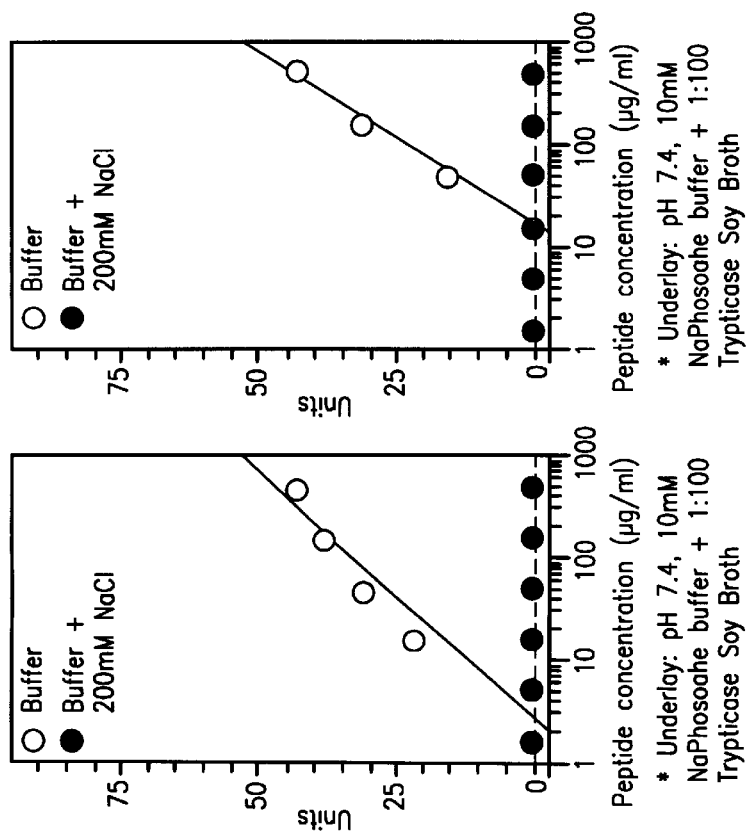

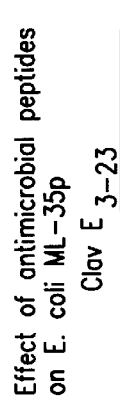
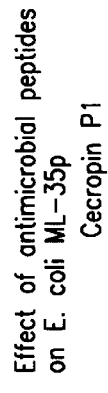
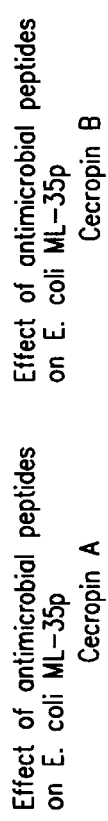
FIG. 11M — Effect of antimicrobial peptides on E. coli ML-35p, Cecropin A
FIG. 11N — Effect of antimicrobial peptides on E. coli ML-35p, Cecropin B
FIG. 11O — Effect of antimicrobial peptides on E. coli ML-35p, Cecropin P1
FIG. 11P — Effect of antimicrobial peptides on E. coli ML-35p, Clav E$_{3-23}$

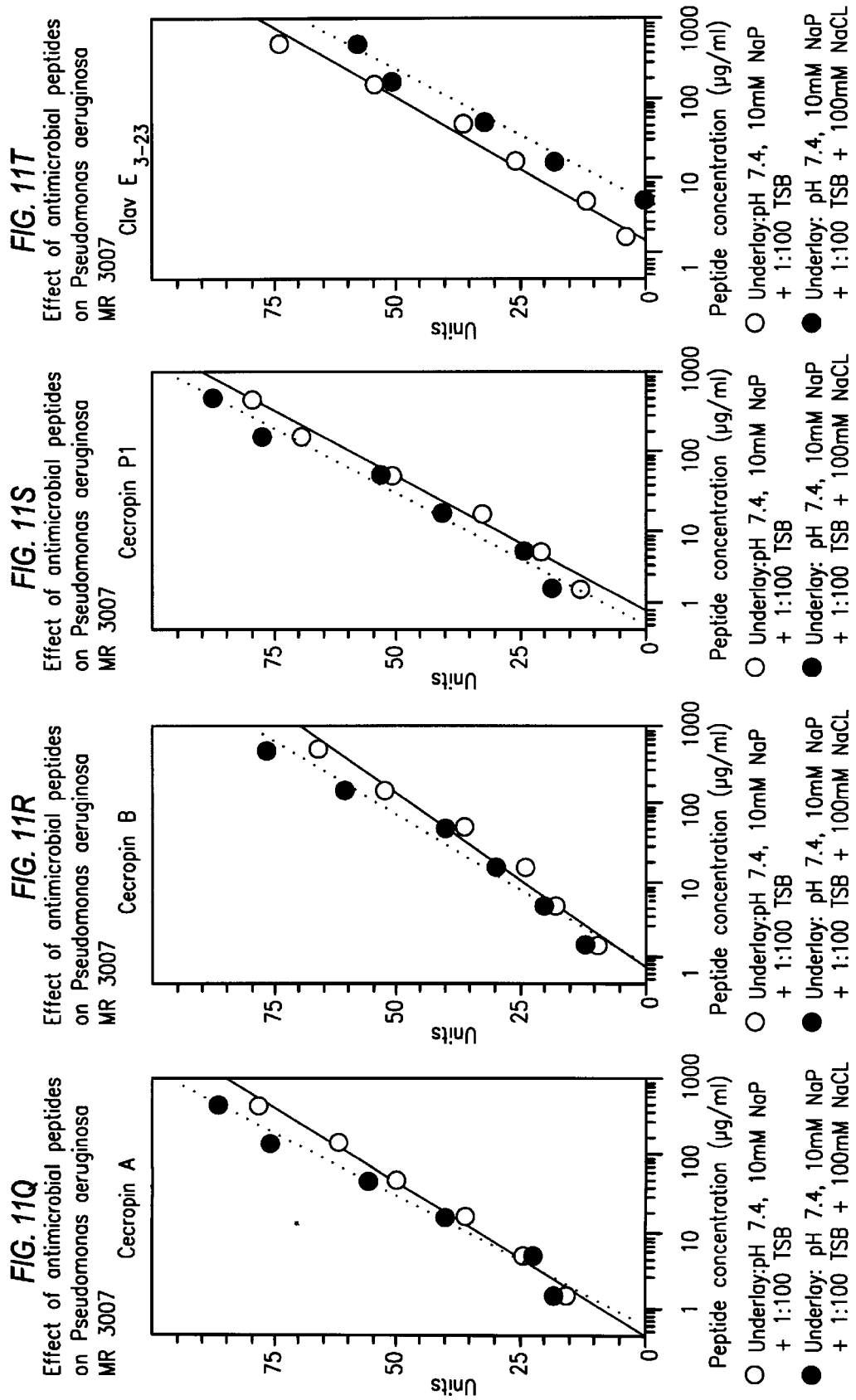

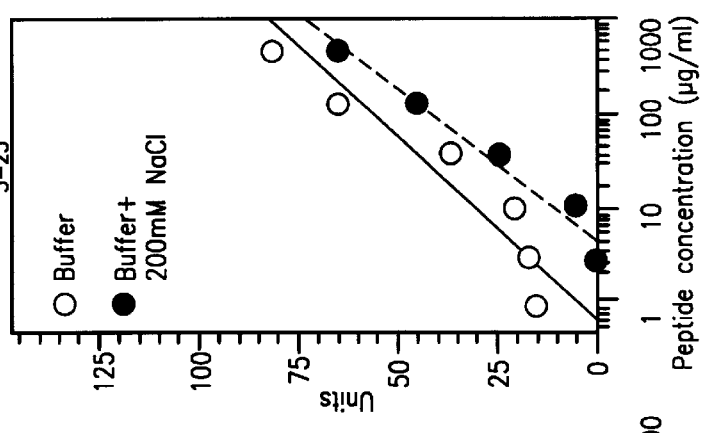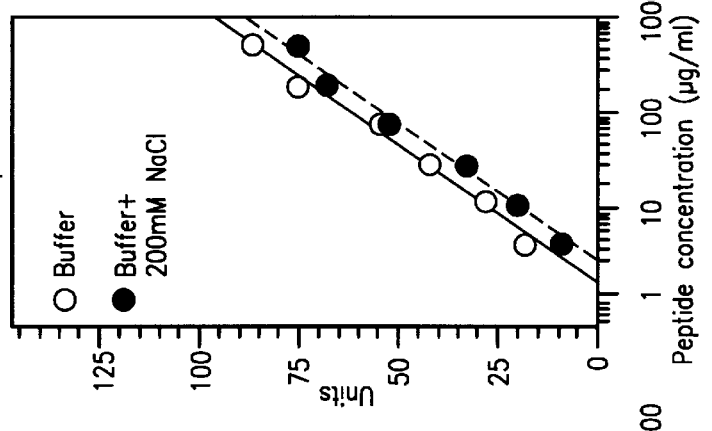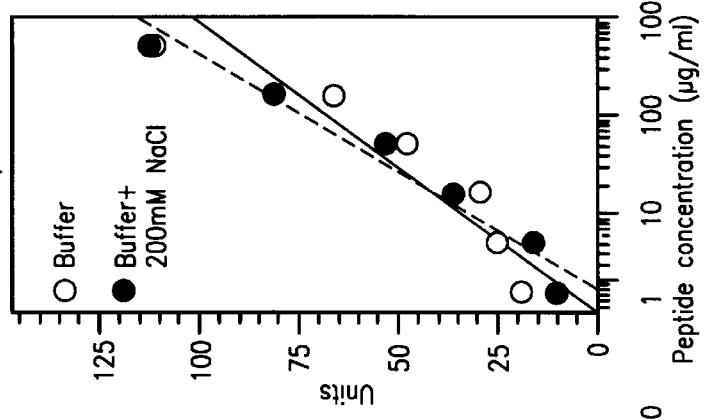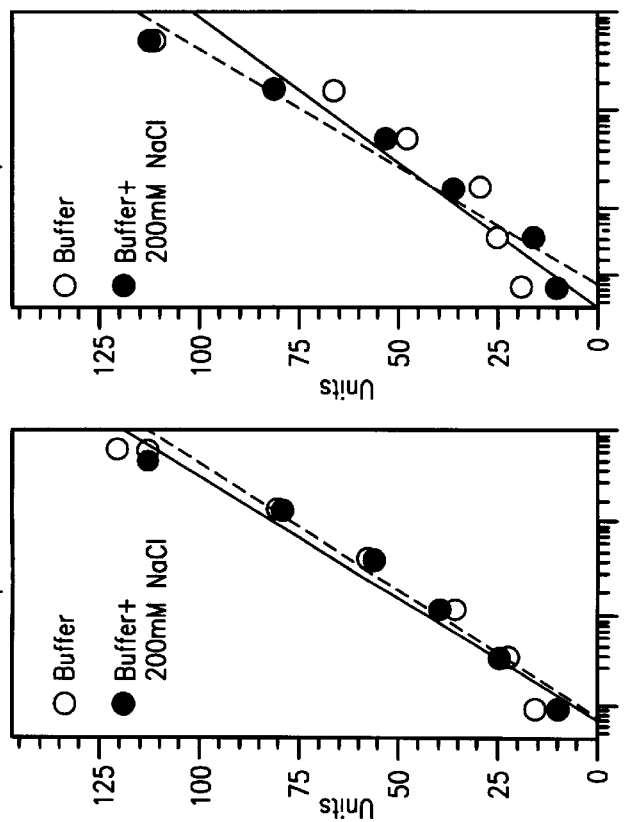

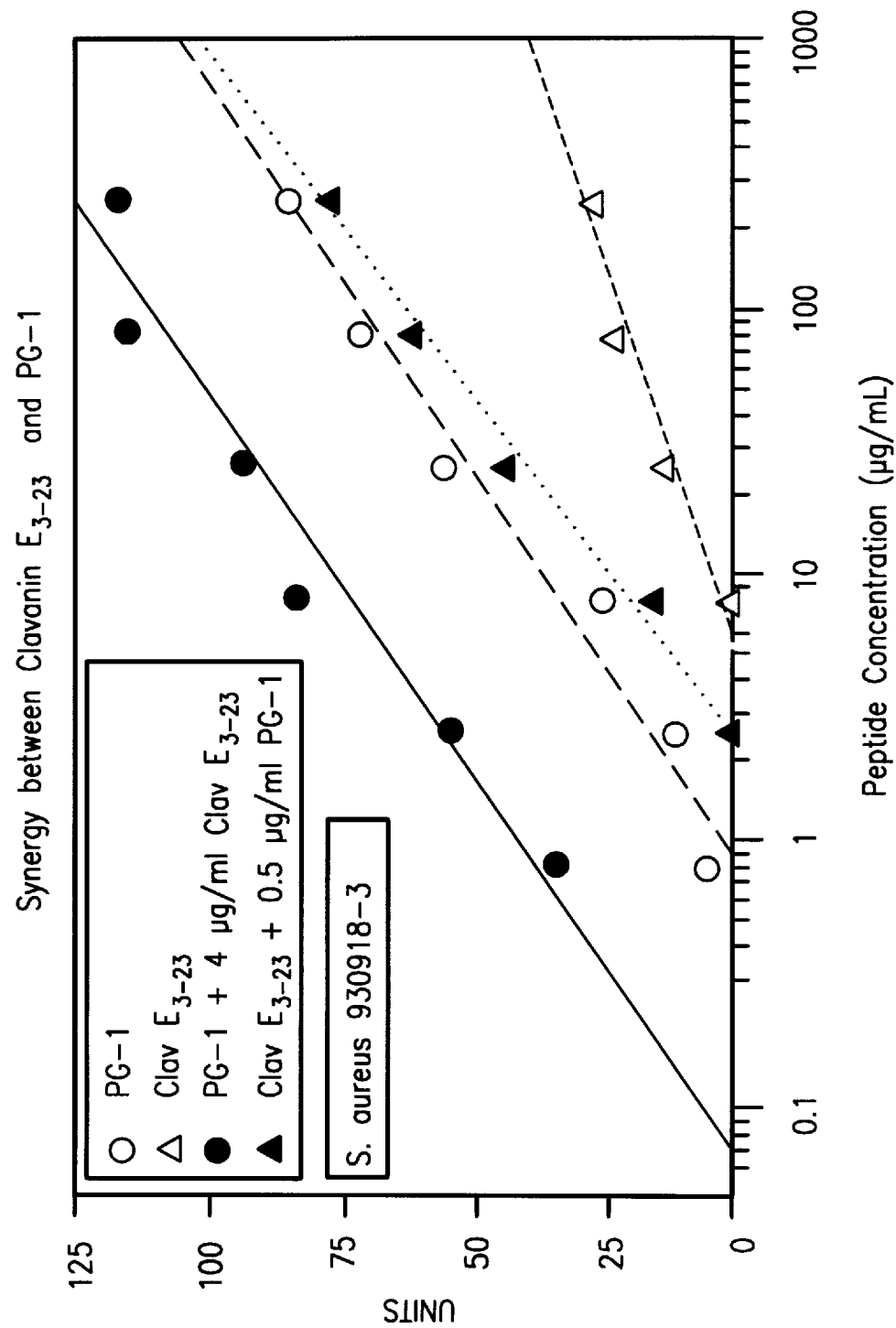

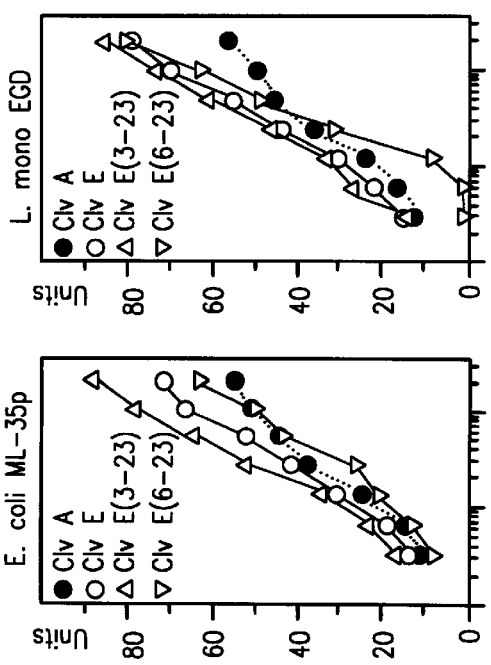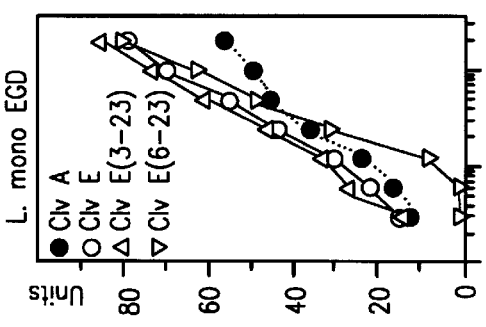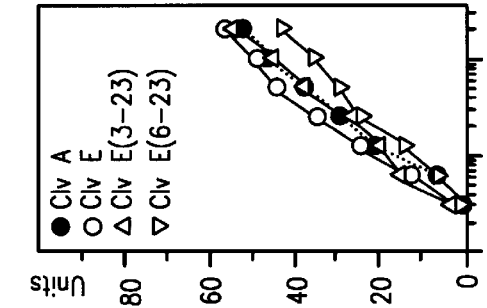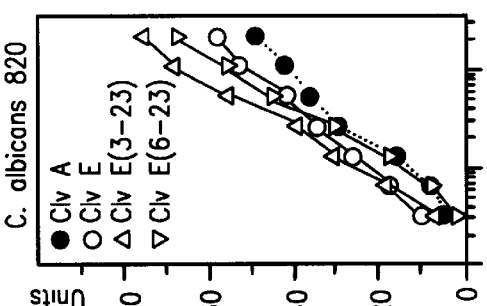

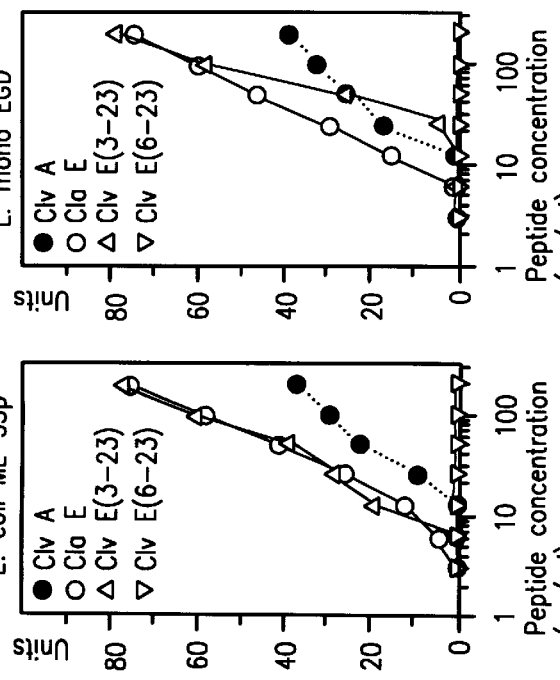
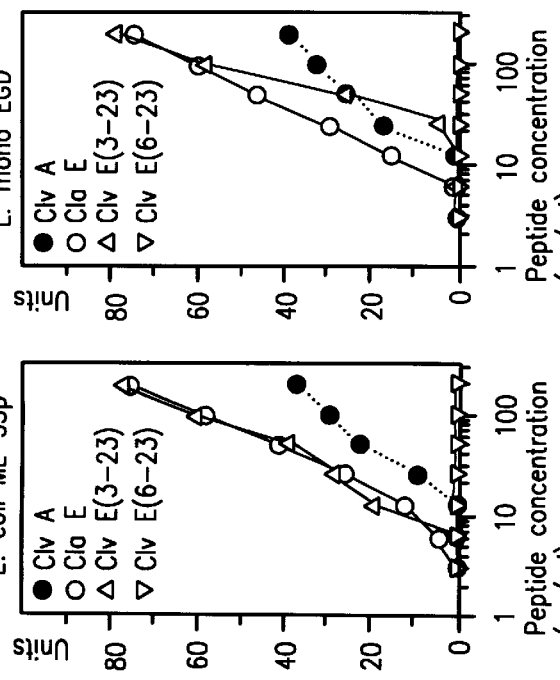
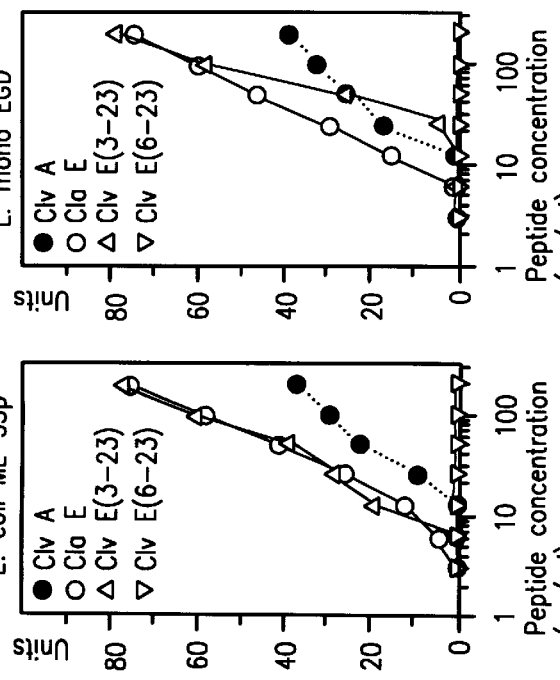
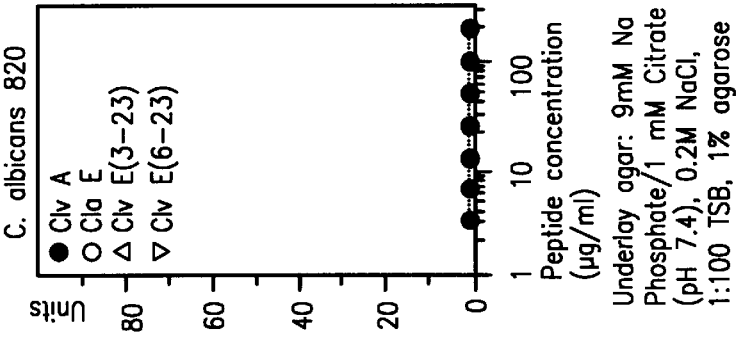
FIG. 13F  FIG. 13G  FIG. 13H  FIG. 13I  FIG. 13J

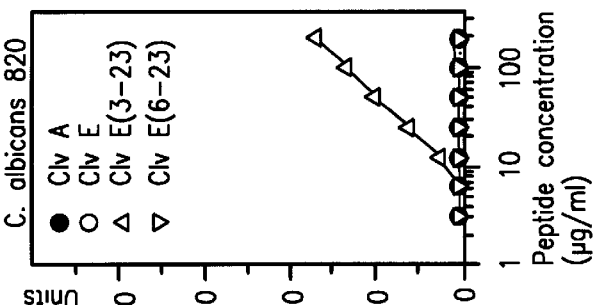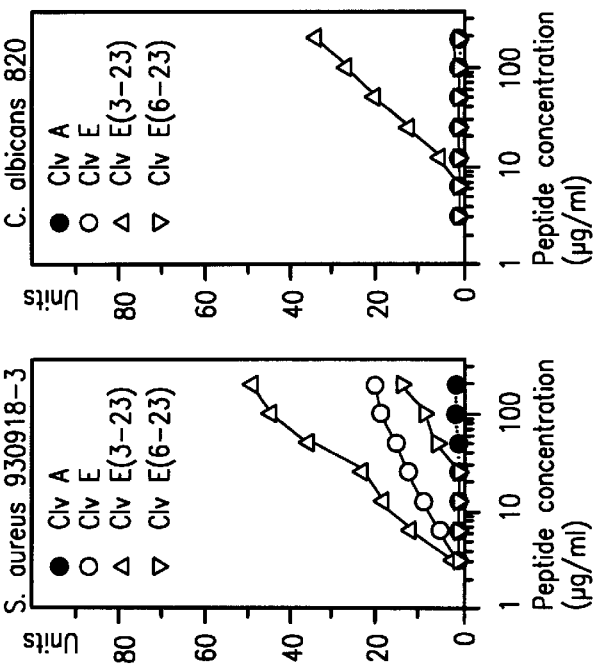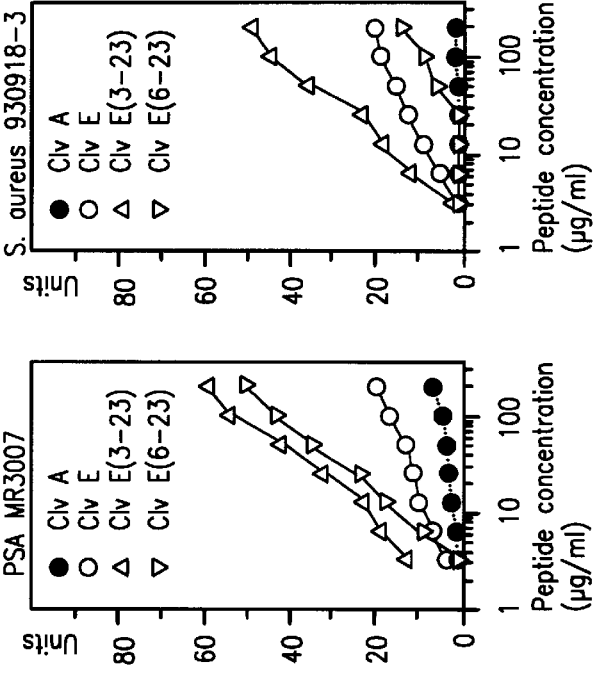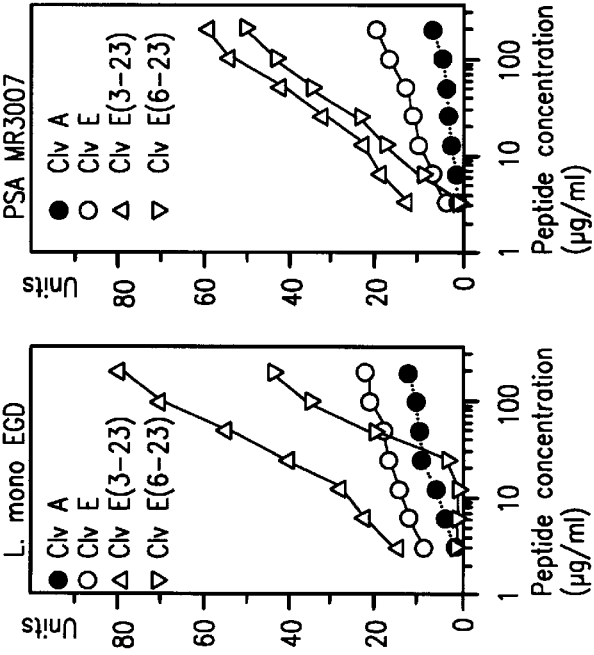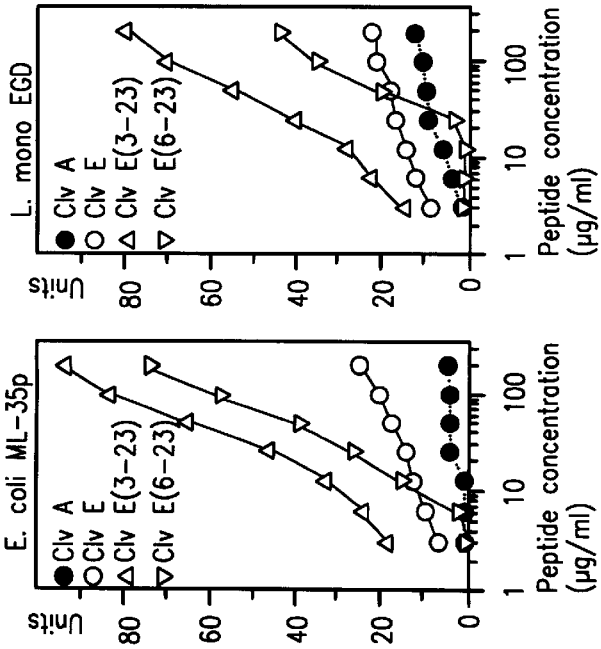

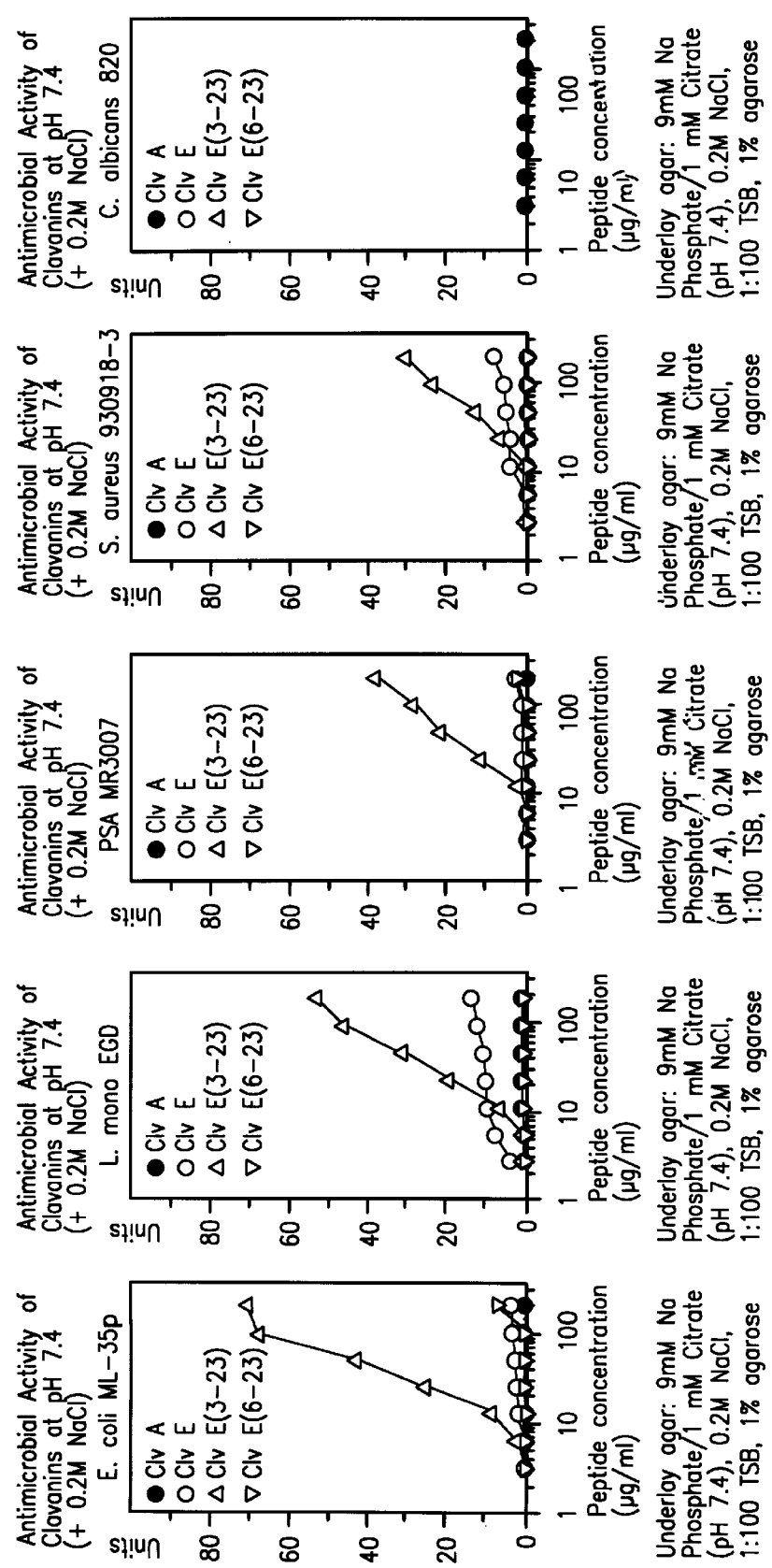

6,040,293

SEQUENCE LISTING

<160> NUMBER OF SEQ ID NOS: 52

<210> SEQ ID NO 1
<211> LENGTH: 23
<212> TYPE: PRT
<213> ORGANISM: Styela clava
<220> FEATURE:
<221> NAME/KEY: SITE
<222> LOCATION: (1)
<223> OTHER INFORMATION: Xaa is a small or a hydrophobic amino acid
      residue selected from the group consisting of Gly, Ser,
      Ala, Thr, Tyr, Val, Ile, Leu, Met, Phe and Trp.
<220> FEATURE:
<221> NAME/KEY: SITE
<222> LOCATION: (2)
<223> OTHER INFORMATION: Xaa is a hydrophobic amino acid residue
      selected from the group consisting of Tyr, Val, Ile,
      Leu, Met, Phe, and Trp.
<220> FEATURE:
<221> NAME/KEY: SITE
<222> LOCATION: (3)
<223> OTHER INFORMATION: Xaa is basic or a polar/large amino acid
      residue selected from the group consisting of Arg, Lys
      His, Asn, and Gln.
<220> FEATURE:
<221> NAME/KEY: SITE
<222> LOCATION: (4)
<223> OTHER INFORMATION: Xaa is a hydrophobic amino acid residue
      selected from the group consisting of Tyr, Val, Ile,
      Leu, Met, Phe, and Trp.
<220> FEATURE:
<221> NAME/KEY: SITE
<222> LOCATION: (5)
<223> OTHER INFORMATION: Xaa is a hydrophobic amino acid residue
      selected from the group consisting of Tyr, Val, Ile,
      Leu, Met, Phe, and Trp.
<220> FEATURE:
<221> NAME/KEY: SITE
<222> LOCATION: (6)
<223> OTHER INFORMATION: Xaa is a small amino acid residue selected from
      the group consisting of Gly, Ser, Ala, and Thr.

-continued

```
<220> FEATURE:
<221> NAME/KEY: SITE
<222> LOCATION: (7)
<223> OTHER INFORMATION: Xaa is a basic amino acid residue selected from
      the group consisting of Arg, Lys and His.
<220> FEATURE:
<221> NAME/KEY: SITE
<222> LOCATION: (8)
<223> OTHER INFORMATION: Xaa is a hydrophobic amino acid residue
      selected from the group consisting of Tyr, Val, Ile,
      Leu, Met, Phe, and Trp.
<220> FEATURE:
<221> NAME/KEY: SITE
<222> LOCATION: (9)
<223> OTHER INFORMATION: Xaa is a hydrophobic amino acid residue
      selected from the group consisting of Tyr, Val, Ile,
      Leu, Met, Phe, and Trp.
<220> FEATURE:
<221> NAME/KEY: SITE
<222> LOCATION: (10)
<223> OTHER INFORMATION: Xaa is a basic amino acid residue selected from
      the group consisting of Arg, Lys and His.
<220> FEATURE:
<221> NAME/KEY: SITE
<222> LOCATION: (11)
<223> OTHER INFORMATION: Xaa is a basic amino acid residue selected from
      the group consisting of Arg, Lys and His.
<220> FEATURE:
<221> NAME/KEY: SITE
<222> LOCATION: (12)
<223> OTHER INFORMATION: Xaa is a hydrophobic amino acid residue
      selected from the group consisting of Tyr, Val, Ile,
      Leu, Met, Phe, and Trp.
<220> FEATURE:
<221> NAME/KEY: SITE
<222> LOCATION: (13)
<223> OTHER INFORMATION: Xaa is a small amino acid residue selected from
      the group consisting of Gly, Ser, Ala, and Thr.
<220> FEATURE:
<221> NAME/KEY: SITE
<222> LOCATION: (14)
<223> OTHER INFORMATION: Xaa is a polar/large amino acid residue
      selected from the group consisting of Asn and Gln.
<220> FEATURE:
<221> NAME/KEY: SITE
<222> LOCATION: (15)
<223> OTHER INFORMATION: Xaa is a hydrophobic amino acid residue
      selected from the group consisting of Tyr, Val, Ile,
      Leu, Met, Phe, and Trp.
<220> FEATURE:
<221> NAME/KEY: SITE
<222> LOCATION: (16)
<223> OTHER INFORMATION: Xaa is a hydrophobic amino acid residue
      selected from the group consisting of Tyr, Val, Ile,
      Leu, Met, Phe, and Trp.
<220> FEATURE:
<221> NAME/KEY: SITE
<222> LOCATION: (17)
<223> OTHER INFORMATION: Xaa is a basic or hydrophobic amino acid
      residue selected from the group consisting of Arg, Lys,
      His, Tyr, Val, Ile, Leu, Met, Phe, and Trp.
<220> FEATURE:
<221> NAME/KEY: SITE
<222> LOCATION: (18)
<223> OTHER INFORMATION: Xaa is a small amino acid residue selected from
      the group consisting of Gly, Ser, Ala, and Thr.
<220> FEATURE:
<221> NAME/KEY: SITE
<222> LOCATION: (19)
<223> OTHER INFORMATION: Xaa is a hydrophobic amino acid residue
      selected from the group consisting of Tyr, Val, Ile,
      Leu, Met, Phe, and Trp.
<220> FEATURE:
<221> NAME/KEY: SITE
<222> LOCATION: (20)
<223> OTHER INFORMATION: Xaa is a small amino acid residue selected from
      the group consisting of Gly, Ser, Ala, and Thr.
<220> FEATURE:
<221> NAME/KEY: SITE
```

```
<222> LOCATION: (21)
<223> OTHER INFORMATION: Xaa is a basic amino acid residue selected from
      the group consisting of Arg, Lys and His.
<220> FEATURE:
<221> NAME/KEY: SITE
<222> LOCATION: (22)
<223> OTHER INFORMATION: Xaa is a hydrophobic amino acid residue
      selected from the group consisting of Tyr, Val, Ile,
      Leu, Met, Phe, and Trp.
<220> FEATURE:
<221> NAME/KEY: SITE
<222> LOCATION: (23)
<223> OTHER INFORMATION: Xaa is a hydrophobic amino acid residue
      selected from the group consisting of Tyr, Val, Ile,
      Leu, Met, Phe, and Trp.

<400> SEQUENCE: 1

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa
            20

<210> SEQ ID NO 2
<211> LENGTH: 360
<212> TYPE: DNA
<213> ORGANISM: Styela clava

<400> SEQUENCE: 2
acaaacaaca ggaaagatga aaacaacaat tttgattctt ctcatactgg gacttggcat     60
caatgcaaaa tctctggagg aaagaaaatc ggaggaagag aaagtattcc aattccttgg   120
caaaattatt catcatgttg gcaattttgt acatggtttt agccacgtgt cggcgacga    180 ccaacaagat aatggaaagt tttatggcca ctacgcagaa gacaatggca agcattggta   240
tgataccggg gatcaataaa aagttttaa acagctacgc gacttgaaga cggacggacc   300
cggcagaaca ttgatatttc ttgttttctt tgattaaagg ctagccttat tactcagaat   360

<210> SEQ ID NO 3
<211> LENGTH: 388
<212> TYPE: DNA
<213> ORGANISM: Styela clava

<400> SEQUENCE: 3
caaactcaga caaacaacag gaaagatgaa acaacaattt tgattcttc tcatactggg     60 acttggcatc aatgcaaaat ctctggagga agaaaatcg gaggaagaaa agtattcca    120 tctccttggc aaaattattc atcatgttgg caattttgta tatggtttta gccacgtgtt   180
cggcgacgac caacaagata atggaaagtt ttatggccac tacgcagaag acaatggcaa   240
gcattggtat gataccgggg atcaataaaa agttttaaa cagctacgcg acttgaagac    300
ggacggaccc ggcagaacat tgatatttct tgttttcttt gattaaaggc tagccttatt   360
actcagaata taacactaca ttgcattc                                      388

<210> SEQ ID NO 4
<211> LENGTH: 356
<212> TYPE: DNA
<213> ORGANISM: Styela clava

<400> SEQUENCE: 4
cagacaaaca acaggaaaga tgaaaacaac aattttgatt cttctcatac tgggacttgg     60
catcaatgca aaatctctgg aggaaagaaa atcggaggaa gagaaagctt tcaaactcct   120
tggcagaatt attcatcatg ttggcaattt tgtatatggt tttagccacg tgttcggcga   180
```

```
cgaccaacaa gataatggaa agttttatgg ccactacgca gaagacaatg gcaagcattg    240
gtatgatacc ggggatcaat aaaaaagttt taaacagcta cgcgacttga agacggacgg    300
acccggcaga acattgatat ttcttgtttt ctttgattaa aggctagcct tattac        356

<210> SEQ ID NO 5
<211> LENGTH: 312
<212> TYPE: DNA
<213> ORGANISM: Styela clava

<400> SEQUENCE: 5
caaactcaga caaacaacag gaaagatgaa acaacaatt ttgattcttc tcatactggg     60
acttggcatc aatgcaaaat ctctggagga agaaaatcg gaggaagaga aattattcaa    120
actccttggc aaaattattc atcatgttgg caattttgta catggtttta gccacgtgtt   180
cggcgacgac caacaagata atggaaagtt ttatggctac tacgcagaag acaatggcaa   240
gcattggtat gataccgggg atcaataaaa aagttttaaa cagctacgcg acttgaagac   300
ggacggaccc gg                                                        312

<210> SEQ ID NO 6
<211> LENGTH: 23
<212> TYPE: PRT
<213> ORGANISM: Styela clava

<400> SEQUENCE: 6

Val Phe Asn Phe Leu Gly Lys Ile Ile His His Val Gly Asn Phe Val
 1               5                  10                  15

Lys Gly Phe Ser His Val Phe
            20

<210> SEQ ID NO 7
<211> LENGTH: 23
<212> TYPE: PRT
<213> ORGANISM: Styela clava

<400> SEQUENCE: 7

Ile Phe Gln Phe Leu Gly Lys Ile Ile His Lys Val Gly Asn Phe Ile
 1               5                  10                  15

His Gly Phe Ser Lys Val Phe
            20

<210> SEQ ID NO 8
<211> LENGTH: 23
<212> TYPE: PRT
<213> ORGANISM: Styela clava

<400> SEQUENCE: 8

Val Phe His Phe Leu Gly Lys Ile Ile His His Val Gly Asn Phe Val
 1               5                  10                  15

Lys Gly Phe Ser His Val Phe
            20

<210> SEQ ID NO 9
<211> LENGTH: 23
<212> TYPE: PRT
<213> ORGANISM: Styela clava

<400> SEQUENCE: 9

Val Phe Gln Phe Leu Gly Lys Ile Ile Lys His Val Gly Asn Phe Leu
 1               5                  10                  15
```

-continued

His Gly Phe Ser His Val Phe
            20

<210> SEQ ID NO 10
<211> LENGTH: 23
<212> TYPE: PRT
<213> ORGANISM: Styela clava

<400> SEQUENCE: 10

Val Phe Lys Phe Leu Gly Lys Ile Val His Lys Val Gly Asn Phe Val
 1               5                  10                  15

Lys Gly Phe Ser Arg Val Phe
            20

<210> SEQ ID NO 11
<211> LENGTH: 23
<212> TYPE: PRT
<213> ORGANISM: Styela clava

<400> SEQUENCE: 11

Leu Phe Gln Phe Leu Gly Lys Ile Ile His His Val Gly Asn Phe Ile
 1               5                  10                  15

His Gly Phe Ser His Val Tyr
            20

<210> SEQ ID NO 12
<211> LENGTH: 23
<212> TYPE: PRT
<213> ORGANISM: Styela clava

<400> SEQUENCE: 12

Val Phe Gln Phe Leu Gly Lys Leu Ile His His Val Gly Asn Phe Val
 1               5                  10                  15

His Gly Phe Ser Lys Val Phe
            20

<210> SEQ ID NO 13
<211> LENGTH: 23
<212> TYPE: PRT
<213> ORGANISM: Styela clava

<400> SEQUENCE: 13

Ile Phe Gln Phe Leu Gly Lys Ile Val His Lys Val Gly Gln Phe Leu
 1               5                  10                  15

His Gly Phe Ser Lys Val Phe
            20

<210> SEQ ID NO 14
<211> LENGTH: 23
<212> TYPE: PRT
<213> ORGANISM: Styela clava

<400> SEQUENCE: 14

Val Phe Arg Phe Leu Gly Lys Ile Val His Val Gly Asn Phe Val
 1               5                  10                  15

Arg Gly Phe Ser His Val Phe
            20

<210> SEQ ID NO 15
<211> LENGTH: 23
<212> TYPE: PRT
<213> ORGANISM: Styela clava

```
<400> SEQUENCE: 15

Ser Phe Gln Phe Leu Gly Lys Ile Ile Lys His Val Gly Asn Phe Leu
  1               5                  10                  15

Lys Gly Tyr Ser Arg Val Phe
            20

<210> SEQ ID NO 16
<211> LENGTH: 23
<212> TYPE: PRT
<213> ORGANISM: Styela clava

<400> SEQUENCE: 16

Val Phe Gln Phe Leu Gly Lys Ile Leu His His Val Gly Asn Phe Val
  1               5                  10                  15

His Ser Phe Ser His Leu Phe
            20

<210> SEQ ID NO 17
<211> LENGTH: 23
<212> TYPE: PRT
<213> ORGANISM: Styela clava

<400> SEQUENCE: 17

Val Phe Lys Phe Leu Gly Lys Ile Ile Arg Lys Val Gly Asn Phe Val
  1               5                  10                  15

His Ala Phe Ser Lys Val Phe
            20

<210> SEQ ID NO 18
<211> LENGTH: 23
<212> TYPE: PRT
<213> ORGANISM: Styela clava

<400> SEQUENCE: 18

Ala Phe Gln Phe Leu Gly Lys Ile Leu Lys Arg Val Gly Asn Phe Leu
  1               5                  10                  15

Lys Gly Phe Ser His Val Tyr
            20

<210> SEQ ID NO 19
<211> LENGTH: 23
<212> TYPE: PRT
<213> ORGANISM: Styela clava

<400> SEQUENCE: 19

Val Phe Gln Phe Leu Gly Lys Ile Ile Lys His Val Gly Asn Phe Val
  1               5                  10                  15

His Gly Phe Ser Arg Val Phe
            20

<210> SEQ ID NO 20
<211> LENGTH: 23
<212> TYPE: PRT
<213> ORGANISM: Styela clava

<400> SEQUENCE: 20

Ala Phe Gln Phe Leu Gly Lys Ile Ile His His Val Gly Asn Phe Ile
  1               5                  10                  15

Lys Gly Phe Ser Lys Val Phe
            20
```

<210> SEQ ID NO 21
<211> LENGTH: 23
<212> TYPE: PRT
<213> ORGANISM: Styela clava

<400> SEQUENCE: 21

Val Phe Lys Phe Leu Gly Lys Val Ile His His Val Gly Gln Phe Val
 1               5                  10                  15

His Gly Phe Ser His Val Phe
            20

<210> SEQ ID NO 22
<211> LENGTH: 23
<212> TYPE: PRT
<213> ORGANISM: Styela clava

<400> SEQUENCE: 22

Val Phe Gln Phe Leu Gly Lys Ile Ile Lys His Val Ala Gln Phe Leu
 1               5                  10                  15

His Gly Phe Ser Arg Val Phe
            20

<210> SEQ ID NO 23
<211> LENGTH: 23
<212> TYPE: PRT
<213> ORGANISM: Styela clava

<400> SEQUENCE: 23

Val Phe His Phe Leu Gly Lys Ile Ile His His Val Gly Asn Phe Val
 1               5                  10                  15

Lys Gly Phe Ser His Val Trp
            20

<210> SEQ ID NO 24
<211> LENGTH: 23
<212> TYPE: PRT
<213> ORGANISM: Styela clava

<400> SEQUENCE: 24

Ile Phe Gln Phe Leu Gly Lys Ile Leu Lys Leu Val Gly Asn Phe Val
 1               5                  10                  15

His Gly Phe Gly His Val Phe
            20

<210> SEQ ID NO 25
<211> LENGTH: 23
<212> TYPE: PRT
<213> ORGANISM: Styela clava

<400> SEQUENCE: 25

Val Phe Gln Phe Leu Gly Lys Ile Ile His Lys Val Gly Asn Tyr Val
 1               5                  10                  15

Arg Gly Phe Ser Lys Val Phe
            20

<210> SEQ ID NO 26
<211> LENGTH: 23
<212> TYPE: PRT
<213> ORGANISM: Styela clava

<400> SEQUENCE: 26

-continued

Gly Phe Lys Phe Leu Gly Lys Val Ile His His Val Ala Asn Trp Leu
 1               5                  10                  15

His Gly Phe Ser Lys Val Phe
            20

<210> SEQ ID NO 27
<211> LENGTH: 23
<212> TYPE: PRT
<213> ORGANISM: Styela clava

<400> SEQUENCE: 27

Leu Phe Gln Phe Leu Gly Lys Ile Ile Lys His Val Ser Asn Phe Val
 1               5                  10                  15

Lys Gly Phe Ser His Val Phe
            20

<210> SEQ ID NO 28
<211> LENGTH: 23
<212> TYPE: PRT
<213> ORGANISM: Styela clava

<400> SEQUENCE: 28

Val Phe Arg Phe Leu Gly Lys Ile Ile Lys Val Gly Asn Phe Val
 1               5                  10                  15

His Gly Phe Ala Lys Val Phe
            20

<210> SEQ ID NO 29
<211> LENGTH: 23
<212> TYPE: PRT
<213> ORGANISM: Styela clava

<400> SEQUENCE: 29

Ser Phe Gln Phe Leu Gly Lys Ile Ile Arg Lys Val Gly Gln Phe Ile
 1               5                  10                  15

His Gly Phe Gly His Val Phe
            20

<210> SEQ ID NO 30
<211> LENGTH: 23
<212> TYPE: PRT
<213> ORGANISM: Styela clava

<400> SEQUENCE: 30

Val Phe Gln Phe Leu Gly Lys Ile Val His Lys Val Ala Asn Phe Leu
 1               5                  10                  15

His Gly Phe Ser His Val Trp
            20

<210> SEQ ID NO 31
<211> LENGTH: 23
<212> TYPE: PRT
<213> ORGANISM: Styela clava

<400> SEQUENCE: 31

Val Phe Asn Phe Leu Gly Lys Ile Ile Arg Arg Val Gly Asn Phe Val
 1               5                  10                  15

Lys Gly Phe Ser Arg Val Phe
            20

<210> SEQ ID NO 32
<211> LENGTH: 23

```
<212> TYPE: PRT
<213> ORGANISM: Styela clava

<400> SEQUENCE: 32

Ala Phe Lys Phe Leu Gly Lys Leu Ile His His Val Gly Asn Phe Ile
 1               5                  10                  15

His Gly Phe Gly His Val Tyr
            20

<210> SEQ ID NO 33
<211> LENGTH: 23
<212> TYPE: PRT
<213> ORGANISM: Styela clava

<400> SEQUENCE: 33

Val Phe Gln Phe Leu Gly Lys Ile Ile Arg Lys Val Gly Asn Phe Val
 1               5                  10                  15

Lys Gly Phe Ser Lys Val Tyr
            20

<210> SEQ ID NO 34
<211> LENGTH: 23
<212> TYPE: PRT
<213> ORGANISM: Styela clava

<400> SEQUENCE: 34

Val Phe Asn Phe Leu Gly Lys Ile Ile His Lys Val Gly Asn Phe Val
 1               5                  10                  15

His Gly Phe Ser Lys Val Phe
            20

<210> SEQ ID NO 35
<211> LENGTH: 23
<212> TYPE: PRT
<213> ORGANISM: Styela clava

<400> SEQUENCE: 35

Ala Phe Gln Phe Leu Gly Lys Ile Val His His Val Gly Asn Phe Leu
 1               5                  10                  15

His Gly Phe Ala His Val Trp
            20

<210> SEQ ID NO 36
<211> LENGTH: 23
<212> TYPE: PRT
<213> ORGANISM: Styela clava
<220> FEATURE:
<221> NAME/KEY: SITE
<222> LOCATION: (1)
<223> OTHER INFORMATION: Xaa is Ala, Leu or Val
<220> FEATURE:
<221> NAME/KEY: SITE
<222> LOCATION: (3)
<223> OTHER INFORMATION: Xaa is Gln, His or Lys
<220> FEATURE:
<221> NAME/KEY: SITE
<222> LOCATION: (4)
<223> OTHER INFORMATION: Xaa is Leu or Phe
<220> FEATURE:
<221> NAME/KEY: SITE
<222> LOCATION: (7)
<223> OTHER INFORMATION: Xaa is Arg or Lys
<220> FEATURE:
<221> NAME/KEY: SITE
<222> LOCATION: (10)
<223> OTHER INFORMATION: Xaa is His or Lys
<220> FEATURE:
```

```
<221> NAME/KEY: SITE
<222> LOCATION: (11)
<223> OTHER INFORMATION: Xaa is His or Lys
<220> FEATURE:
<221> NAME/KEY: SITE
<222> LOCATION: (17)
<223> OTHER INFORMATION: Xaa is His, Lys or modified Tyr
<220> FEATURE:
<221> NAME/KEY: SITE
<222> LOCATION: (21)
<223> OTHER INFORMATION: Xaa is His or Lys

<400> SEQUENCE: 36

Xaa Phe Xaa Xaa Lys Gly Xaa Ile Ile Xaa Xaa Val Gly Asp Phe Val
 1               5                  10                  15

Xaa Gly Phe Ser Xaa Val Phe
            20

<210> SEQ ID NO 37
<211> LENGTH: 23
<212> TYPE: PRT
<213> ORGANISM: Styela clava

<400> SEQUENCE: 37

Gly Ile Gly Lys Phe Leu His Ser Ala Gly Lys Phe Gly Lys Ala Phe
 1               5                  10                  15

Val Gly Glu Ile Met Lys Ser
            20

<210> SEQ ID NO 38
<211> LENGTH: 23
<212> TYPE: PRT
<213> ORGANISM: Styela clava

<400> SEQUENCE: 38

Gly Ile Gly Lys Phe Leu Lys Ser Ala Gly Lys Phe Gly Lys Ala Phe
 1               5                  10                  15

Val Asn Glu Ile Met Lys Ser
            20

<210> SEQ ID NO 39
<211> LENGTH: 23
<212> TYPE: PRT
<213> ORGANISM: Styela clava

<400> SEQUENCE: 39

Val Phe Gln Phe Leu Gly Lys Ile Ile His His Val Gly Asn Phe Val
 1               5                  10                  15

His Gly Phe Ser His Val Phe
            20

<210> SEQ ID NO 40
<211> LENGTH: 23
<212> TYPE: PRT
<213> ORGANISM: Styela clava

<400> SEQUENCE: 40

Val Phe Gln Phe Leu Gly Arg Ile Ile His His Val Gly Asn Phe Val
 1               5                  10                  15

His Gly Phe Ser His Val Phe
            20

<210> SEQ ID NO 41
<211> LENGTH: 23
```

<212> TYPE: PRT
<213> ORGANISM: Styela clava
<220> FEATURE:
<221> NAME/KEY: SITE
<222> LOCATION: (17)
<223> OTHER INFORMATION: Wherein Xaa is a modified Tyr.

<400> SEQUENCE: 41

Val Phe His Leu Leu Gly Lys Ile Ile His His Val Gly Asn Phe Val
 1               5                  10                  15

Xaa Gly Phe Ser His Val Phe
            20

<210> SEQ ID NO 42
<211> LENGTH: 23
<212> TYPE: PRT
<213> ORGANISM: Styela clava
<220> FEATURE:
<221> NAME/KEY: SITE
<222> LOCATION: (17)
<223> OTHER INFORMATION: Wherein Xaa is a modified Tyr.

<400> SEQUENCE: 42

Ala Phe Lys Leu Leu Gly Arg Ile Ile His His Val Gly Asn Phe Val
 1               5                  10                  15

Xaa Gly Phe Ser His Val Phe
            20

<210> SEQ ID NO 43
<211> LENGTH: 23
<212> TYPE: PRT
<213> ORGANISM: Styela clava

<400> SEQUENCE: 43

Leu Phe Lys Leu Leu Gly Lys Ile Ile His His Val Gly Asn Phe Val
 1               5                  10                  15

His Gly Phe Ser His Val Phe
            20

<210> SEQ ID NO 44
<211> LENGTH: 30
<212> TYPE: DNA
<213> ORGANISM: Styela clava
<220> FEATURE:
<221> NAME/KEY: modified_base
<222> LOCATION: (19)
<223> OTHER INFORMATION: inosine
<220> FEATURE:
<221> NAME/KEY: modified_base
<222> LOCATION: (22)
<223> OTHER INFORMATION: inosine

<400> SEQUENCE: 44
gtcgactagt caycaygtng gnaayttygt                              30

<210> SEQ ID NO 45
<211> LENGTH: 7
<212> TYPE: PRT
<213> ORGANISM: Styela clava

<400> SEQUENCE: 45

His His Val Gly Asn Phe Val
 1               5

<210> SEQ ID NO 46
<211> LENGTH: 11

```
<212> TYPE: PRT
<213> ORGANISM: Styela clava

<400> SEQUENCE: 46

Ser Leu Glu Glu Arg Lys Ser Glu Glu Glu Lys
 1               5                  10

<210> SEQ ID NO 47
<211> LENGTH: 21
<212> TYPE: PRT
<213> ORGANISM: Styela clava
<220> FEATURE:

<400> SEQUENCE: 47

Gln Phe Leu Gly Lys Ile Ile His His Val Gly Asn Phe Val His Gly
 1               5                  10                  15
Phe Ser His Val Phe
            20

<210> SEQ ID NO 48
<211> LENGTH: 21
<212> TYPE: PRT
<213> ORGANISM: Styela clava

<400> SEQUENCE: 48

Gln Phe Leu Gly Arg Ile Ile His Val Gly Asn Phe Val His Gly
 1               5                  10                  15
Phe Ser His Val Phe
            20

<210> SEQ ID NO 49
<211> LENGTH: 21
<212> TYPE: PRT
<213> ORGANISM: Styela clava
<220> FEATURE:
<221> NAME/KEY: SITE
<222> LOCATION: (15)
<223> OTHER INFORMATION: Wherein Xaa is a modified Tyr.

<400> SEQUENCE: 49

His Leu Leu Gly Lys Ile Ile His Val Gly Asn Phe Val Xaa Gly
 1               5                  10                  15
Phe Ser His Val Phe
            20

<210> SEQ ID NO 50
<211> LENGTH: 21
<212> TYPE: PRT
<213> ORGANISM: Styela clava
<220> FEATURE:
<221> NAME/KEY: SITE
<222> LOCATION: (15)
<223> OTHER INFORMATION: Wherein Xaa is a modified Tyr.

<400> SEQUENCE: 50

Lys Leu Leu Gly Arg Ile Ile His Val Gly Asn Phe Val Xaa Gly
 1               5                  10                  15
Phe Ser His Val Phe
            20

<210> SEQ ID NO 51
<211> LENGTH: 21
<212> TYPE: PRT
<213> ORGANISM: Styela clava

<400> SEQUENCE: 51

Lys Leu Leu Gly Lys Ile Ile His Val Gly Asn Phe Val His Gly
 1               5                  10                  15
```

```
Phe Ser His Val Phe
            20

<210> SEQ ID NO 52
<211> LENGTH: 22
<212> TYPE: PRT
<213> ORGANISM: Styela clava

<400> SEQUENCE: 52

Phe Lys Leu Leu Gly Lys Ile Ile His His Val Gly Asn Phe Val His
 1               5                  10                  15
Gly Phe Ser His Val Phe
            20
```

1

CLAVANINS

This is a continuation-in-part of U.S. Ser. No. 08/746,160, filed Nov. 6, 1996 from which priority is claimed, and the contents of which are incorporated herein by reference.

ACKNOWLEDGMENT OF GOVERNMENT SUPPORT

This invention was made at least in part with funding from NIH grant numbers 1-PO1-AI-37945-01 and 5R37-AI-22839-10. The U.S. Government has certain rights in this invention.

TECHNICAL FIELD

The invention relates to a class of peptide and peptide-like compounds with antimicrobial activity. These peptides, designated "clavanins" are characterized by patterns of basic and hydrophobic amino acids which result in compounds with a spectrum of antimicrobial activities.

BACKGROUND ART

Antimicrobial peptides have been isolated from a wide variety of animal sources. These sources include, prominently, leukocytes of humans (Lehrer, R. I. et al., *Ann Rev Immunol* (1992) 11:105); pigs (Kokryakov, V. N. et al., *FEBS Lett* (1993) 231); bovine sources (Selsted, M. E. et al., *J Biol Chem* (1993) 268:6641); rabbits (Patterson-Delafield, J. et al., *Infect Immun* (1980) 30:180); and birds (Harwig, S. S. L. et al., *FEBS Lett* (1994) 342:281). Antimicrobial peptides have also been found in bovine tongue (Schonwetter, B. S. et al., *Science* (1995) 267:1645) respiratory tract epithelia (Diamond, G. et al., *Proc Natl Acad Sci USA* (1991) 88:3952) and gastrointestinal and genital urinary tracts of humans and animals (Jones, D. E. et al., *J Biol Chem* (1992) 267:23216; Bensch, K. W. et al., *FEBS Lett* (1995) 368:331). In addition, antimicrobial peptides have been isolated from the hemocytes of the Horseshoe Crab as described by Nakamura, T. et al., *J Biol Chem* (1988) 263:16709–16713. These various antimicrobial peptides, for example the tachyplesins, polyphemusins, defensins, clavanins and gallinacins, are typically characterized by specific positions of cysteine residues which putatively control conformation of the molecule.

An additional class of antimicrobial peptides, found in the skin of the African clawed frog, *Xenopus laevis*, are α-helical (noncovalent-cyclic) peptides (Zasloff, M., *Proc Natl Acad Sci USA* (1987) 84:5449). This class of antimicrobial peptides, called the magainins, in their mature form contain, 23 amino acids and are α-helical but not amidated. The magainins possess broad spectrum antimicrobial activity (Harwig, S. S. L. et al., *FEBS Lett* (1994) 342:281; Zasloff, M. et al., *Proc Natl Acad Sci USA* (1988) 85:910). The nature of the antimicrobial activity as related to the α-helical amphipathic structure of magainins has been studied (Duclohier, H. et al., *Biophys J* (1989) 56:1017) as has that of another class of α-helical antimicrobial peptides, the cecropins (Christensen, B. et al., *Proc Natl Acad Sci USA* (1988) 85:5072. The magainins are synthesized from a large prepropeptide containing a single copy of Magainin-1 and five copies of the closely related Magainin-2 (Terry, A. S. et al., *J Biol Chem* (1988) 263:5745).

Antimicrobial peptides and proteins have also been found in plants as reviewed by Cornelissen, B. J. C. et al., *Plant Physiol* (1993) 101:709–712.

The present invention is directed to a class of peptides and peptide-like compounds several members of which may be isolated from the hemocytes of the tunicate *Styela clava*. Tunicates are simple marine invertebrates whose larval forms contain a constellation of features establishing their kinship to early vertebrates. The body cavity of the mature tunicate provides an acceptable source of mesoderm-derived phagocytes (hemocytes) that are counterparts to the blood leukocytes of higher vertebrates. It is known that phagocytes of freshly harvested colonial tunicates are often filled with various bacteria and that the introduction of bacteria beneath the tunic is capable of inducing phagocytic cells to traverse the underlying epithelium and surround these foreign objects.

DISCLOSURE OF THE INVENTION

The invention is directed to a class of peptides and peptide-like compounds, the clavanins, that are characterized by specific patterns of basic and hydrophobic amino acid side-chains and which show a broad spectrum of antimicrobial activity. The clavanins are therefore useful additions to the repertoire of agents useful in preserving materials otherwise susceptible to microbial degradation, in protecting plants against bacterial infection, and in therapeutic and prophylactic protection of animals against bacteria, fungi and viruses. As used in the present application "antimicrobial" refers to the ability to inhibit the growth of, destroy, or otherwise impede the undesired destructive effects of such replicable forms.

Thus, in one aspect, the invention is directed to compounds of the formula:(SEQ ID NO:1)

$$X'_1 X_2 B'_3 X_4 X_5 U_6 B_7 X_8 X_9 B_{10} B_{11} X_{12} U_{13} Z_{14} X_{15} X_{16}$$
$$B^*_{17} U_{18} X_{19} U_{20} B_{21} X_{22} X_{23} \qquad (1)$$

wherein X is a hydrophobic amino acid residue or modified form thereof;

X' is a small or a hydrophobic amino acid residue or a modified form thereof;

B is a basic amino acid residue or modified form thereof;

B' is basic or a polar/large amino acid residue or modified form thereof; and

B* is a basic or a hydrophobic amino acid residue or a modified form thereof;

U is a small amino acid residue or modified form thereof;

Z is a polar/large amino acid residue or modified form thereof.

The compounds of formula 1 include those which are truncated by 1–5 amino acids at the N-terminus, as shown by the brackets. Truncation of 1–3 amino acids, preferably 1–2 amino acids are preferred.

Included in the invention are the compounds of formula (1) in the acylated and/or amidated form as well as the esters and salts.

In other aspects, the invention is directed to recombinant materials useful for the production of those peptides of the invention that contain gene-encoded amino acids, as well as plants or animals modified to contain expression systems for the production of these peptides. The invention also includes methods to prepare and manipulate these recombinant materials.

In addition, the invention is directed to pharmaceutical compositions and compositions for application to plants and to materials whose preservation from microbial growth is desired, which compositions contain the compounds of the invention as active ingredients and to compositions which contain expression systems for the production of the peptides for in situ expression of the nucleotide sequence encoding these peptides. The invention is also directed to methods to prepare the invention compounds synthetically, to antibodies specific for these compounds, and to the use of the compounds as preservatives, therapeutics, and prophylactics. The invention is also directed to the use of the compounds of the invention as standards in antimicrobial assays and as affinity ligands for adsorption of counterpart structures in microbes, including viruses, as set forth above.

BRIEF DESCRIPTION OF THE DRAWINGS

FIG. 1 shows reverse-phase HPLC of the clavanin-containing fraction derived from *S. clava* hemocytes. The drawing further includes depictions of further separation of peaks a and b derived from an initial chromatographic run.

FIGS. 3A–3E (SEQ ID NO:2 through SEQ ID NO:5) show sequences of cDNA encoding clavanins A, C, D and E and a comparison of pre- and post-sequences.

FIG. 6 shows antimicrobial activity, against *L. monocytogenes*, of native Clavanin A, synthetic Clavanin A and a modified form of Clavanin A wherein the histidine residues are replaced by lysine (Clavanin A(K)) as a function of pH.

FIG. 7 shows a similar comparison to that of FIG. 6 with respect to *E. coli*.

FIG. 8 shows a similar comparison to that of FIG. 6 with respect to *C. albicans*.

FIG. 9 shows the kinetics of Clavanin A, Clavanin A(K) and comparatively, Cecropin P1 and Magainin 1 in their antimicrobial action against *L. monocytogenes*.

FIGS. 11A–11X show the activity of Clavanin E(3-23) against various microorganisms in comparison with cecropin.

FIGS. 12A, 12B and 12C show the synergistic effects of Clavanin E(3-23) and PG-1 versus *S.aureus, B.cepacia,* and *P.aeruginousa,* respectively.

FIGS. 13A–13J show the antimicrobial activity of various Clavanins at pH 5.5 with and without salt, respectively, against various target organisms.

FIGS. 14A–14J show the antimicrobial activity of Clavanins against various microorganisms at pH7.4 with and without salt, respectively.

MODES OF CARRYING OUT THE INVENTION

Figure 2:
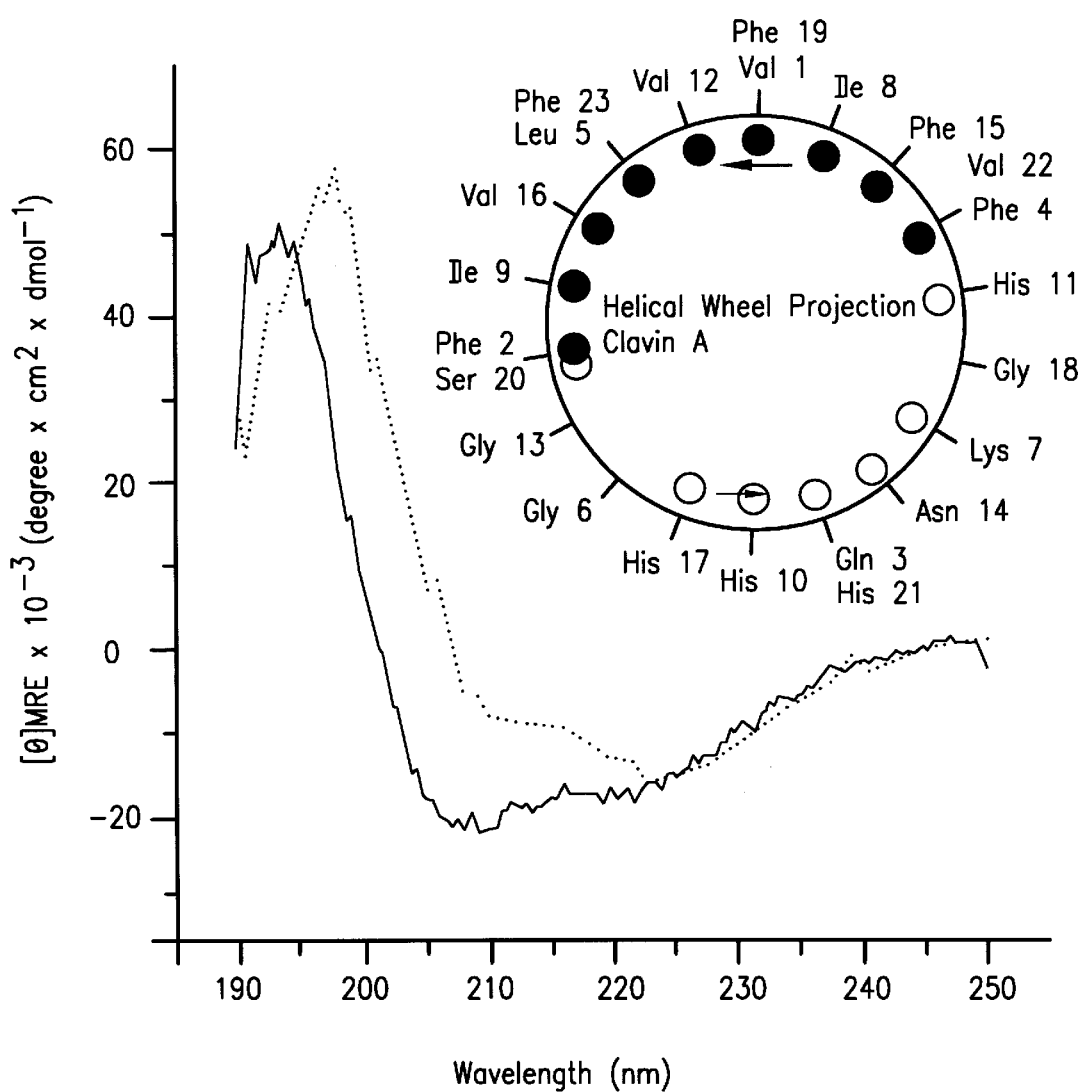
FIG. 2 shows the circular dichroism pattern for Clavanin A and a helical wheel projection of the structure based on these results.

The compounds of the invention are generally described by the formula (SEQ ID NO:1)

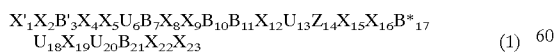
(1)

and the salts, esters, amides, and acyl forms thereof. Each position represented by a letter indicates a single amino acid residue although, as described below, one or more of the peptide linkages between such residues may be replaced by a peptide linkage mimic. The invention compounds include those represented by formula (1) as well as analogous peptides which are isolable from the hemocytes of tunicates. As shown in formula (1), the amino acid sequence may be truncated at the N-terminus by deletion of 1–5 amino acids. Preferably only 1–3 of the N-terminal amino acids are deleted, more preferably 1–2. "Analogous" forms are those which retain the ability to form an α-helical configuration, are antimicrobial, and are linear (rather than disulfide) in configuration/conformation.

The amino terminus of the peptide may be in the free amino form or may be acylated by a group of the formula RCO—, wherein R represents a hydrocarbyl group of 1–6C. The hydrocarbyl group is saturated or unsaturated and is typically, for example, methyl, ethyl, i-propyl, t-butyl, n-pentyl, cyclohexyl, cyclohexene-2-yl, hexene-3-yl, hexyne-4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6C as defined above. Amidated forms of the peptides wherein the C-terminus has the formula $CONH_2$ are preferred.

As the peptides of the invention contain substantial numbers of basic amino acids, the peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood.

The amino acids in the peptides of the invention may be those encoded by the gene or analogs thereof, and may also be the D-isomers thereof. One preferred embodiment of the peptides of the invention is that form wherein all of the residues are in the D-configuration thus conferring resistance to protease activity while retaining antimicrobial or antiviral properties. The resulting clavanins are themselves enantiomers of the native L-amino acid-containing forms.

The amino acid notations used herein are conventional and are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer at the α carbon is intended unless the D-form is expressly indicated by a dagger superscript (†).

The compounds of the invention are peptides or peptide-like compounds which are partially defined in terms of amino acid residues of designated classes. Amino acid residues can be generally subclassified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Neutral/polar: The residues are not charged at physiological pH, but the residue is not sufficiently repelled by aqueous solutions so that it would seek inner positions in the conformation of a peptide in which it is contained when the peptide is in aqueous medium.

This description also characterizes certain amino acids as "small" since their side chains are not sufficiently large, even if polar groups are lacking, to confer hydrophobicity. "Small" amino acids are those with four carbons or less when at least one polar group is on the side chain and three carbons or less when not.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at the relevant pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic.

For the naturally occurring protein amino acids, subclassification according to the foregoing scheme is as follows.

| | |
|---|---|
| Acidic | Aspartic acid and Glutamic acid |
| Basic | Noncyclic: Arginine, Lysine |
| | Cyclic: Histidine |
| Small | Glycine, Serine, Alanine, Threonine |
| Polar/large | Asparagine, Glutamine |
| Hydrophobic | Tyrosine, Valine, Isoleucine, Leucine, Methionine, Phenylalanine, Tryptophan |

The gene-encoded secondary amino acid proline is a special case due to its known effects on the secondary conformation of peptide chains, and is not, therefore, included in a group. Cysteine residues are also not included in these classifications since their capacity to form disulfide bonds to provide secondary structure may override the general polarity/nonpolarity of the residue. However, if a cysteine, which is, technically speaking, a small amino acid, is modified so as to prevent its participation in secondary structure, those locations indicated "S" in the compound of formula (1) may be inhabited by such modified cysteine residues. In addition, a single cysteine residue may occupy a position indicated by "S" although this is less favored because of the possibility of formation of intermolecular disulfides which may denature the antimicrobial activity of the compounds.

The "modified" amino acids that may be included in the clavanins are gene-encoded amino acids which have been processed after translation of the gene, e.g., by the addition of methyl groups or derivatization through covalent linkage to other substituents or oxidation or reduction or other covalent modification. The classification into which the resulting modified amino acid falls will be determined by the characteristics of the modified form. For example, if lysine were modified by acylating the ε-amino group, the modified form would not be classed as basic but as polar/large.

Certain commonly encountered amino acids, which are not encoded by the genetic code, include, for example, beta-alanine (beta-Ala), or other omega-amino acids, such as 3-aminopropionic, 2,3-diaminopropionic (2,3-diaP), 4-aminobutyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); β-2-thienylalanine (Thi); methionine sulfoxide (MSO); and homoarginine (Har). These also fall conveniently into particular categories.

Based on the above definitions,

Sar, beta-Ala and Aib are small;

t-BuA, t-BuG, N-MeIle, Nle, Mvl, Cha, Phg, Nal, Thi and Tic are hydrophobic;

2,3-diaP, Orn and Har are basic;

Cit, Acetyl Lys and MSO are neutral/polar/large.

The various omega-amino acids are classified according to size as small (beta-Ala and 3-aminopropionic) or as large and hydrophobic (all others).

Other amino acid substitutions for those encoded in the gene can also be included in peptide compounds within the scope of the invention and can be classified within this general scheme according to their structure.

In all of the "peptides" of the invention, one or more amide linkages (—CO—NH—) may optionally be replaced with another linkage which is an isostere such as —CH$_2$NH—, —CH$_2$S—, —CH$_2$CH$_2$—, —CH=CH— (cis and trans), —COCH$_2$—, —CH(OH)CH$_2$— and —CH$_2$SO—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—CH$_2$NH—, —CH$_2$CH$_2$—); Spatola, A. F., et al., *Life Sci* (1986) 38:1243–1249 (—CH$_2$—S); Hann, M.

M., *J Chem Soc Perkin Trans I* (1982) 307–314 (—CH—CH—, cis and trans); Almquist, R. G., et al., *J Med Chem* (1980) 23:1392–1398 (—COCH$_2$—); Jennings-White, C., et al., *Tetrahedron Lett* (1982) 23:2533 (—COCH$_2$—); Szelke, M., et al., European Application EP 45665 (1982) CA:97:39405 (1982) (—CH(OH)CH$_2$—); Holladay, M. W., et al., *Tetrahedron Lett* (1983) 24:4401–4404 (—C(OH)CH$_2$—); and Hruby, V. J., *Life Sci* (1982) 31:189–199 (—CH$_2$—S—).

The compounds of formula (1) are generally defined as set forth in the Disclosure of the Invention set forth above.

In preferred embodiments of the compounds of the invention,

X'$_1$ is Val, Leu, Ile, or Ala;

X$_2$ is Phe, Trp or Tyr;

B'$_3$ is Asn, Gln, His, Lys or Arg;

X$_4$ and X$_5$ is each independently selected from the group consisting of Phe, Leu, Tyr, and Val;

S$_6$ is Gly, Ser or Ala, preferably Gly;

B$_7$ is Lys or Arg;

X$_8$ and Xg is each independently selected from the group consisting of Ile, Leu and Val;

B$_{10}$ and B$_{11}$ is each independently His, Lys or Arg, preferably His;

X$_{12}$ is Val, Ile, or Leu;

U$_{13}$ is Ala, Ser or Gly, preferably Gly;

Z$_{14}$ is Asn or Gln;

X$_{15}$ and X$_{16}$ is each independently selected from the group consisting of Phe, Tyr, Trp, Val, Leu and Ile, preferably X$_{15}$ is Phe and X$_{16}$ is Val, Ile or Leu;

B*$_{17}$ is His, Lys, Arg, Trp, Phe or Tyr or a modified form thereof;

U$_{18}$ is Ala, Ser or Gly, preferably Gly;

X$_{19}$ is Phe, Tyr or Trp, preferably Phe;

U$_{20}$ is Gly, Ala or Ser, preferably Ser;

B$_{21}$ is His, Lys or Arg, preferably His; and each of X$_{22}$ and X$_{23}$ is Ile, Val, Leu, Phe, Tyr or Trp, most preferably X$_{22}$ is Val, Ile or Leu and X$_{23}$ is Phe, Tyr or Trp.

Additonal preferred forms of the invention are those wherein 1–5 amino acids at the N-terminus have been deleted; preferably 1–3 amino acids, and more preferably 1–2 amino acids. Deletions of only one amino acid, and four amino acids are also specifically contemplated.

Also especially preferred are the C-terminal amidated forms of the compounds of the invention where the carboxyl terminus is of the formula —CONH$_2$.

Typical compounds within the scope of the clavanins are:(SEQ ID NO:6 through SEQ ID NO:35)

| | | | | |
|---|---|---|---|---|
| VFNFL | GKIIH | HVGNF | VKGFS† | HVF* |
| IFQFL | GKIIH† | KVGNF | IHGFS | KVF* |
| VFHFL | GKIIH | HVGNF | VKGFS | HVF* |
| VFQFL | GKIIK | HVGNF | LHGFS | HVF |
| VFKFL | GKIVH | KVGNF | VKGFS | RVF* |
| LFQFL† | GKIIH† | HVGNF | IHGFS | HVY* |
| VFQFL | GKLIH | HVGNF | VHGFS | KVF* |
| IFQFL | GKIVH | KVGQF | LHGFS | KVF* |
| VFRFL | GKIVH | HVGNF | VRGFS | HVF* |
| SFQFL | GKIIK | HVGNF | LKGYS | RVF* |
| VFQFL | GK†ILH | HVGN†F | VHSFS | HLF |
| VFKFL | GKIIR | KVGNF | VHAFS† | KVF* |
| AFQFL | GKILK | RVGNF | LKGFS | HVY* |
| VFQFL | GKIIK | HVGN†F | VHGFS | RVF* |
| AFQFL | GKIIH | HVGNF | IKGFS | KVF* |
| VFKFL | GKVI†H | HVGQF | VHGFS | HVF* |
| VFQFL† | GKIIK | HVAQF | LHGFS | RVF* |
| VFHFL | GKIIH | HVGNF | VKGFS | HVW* |
| IFQ†FL | GKILK | LVGNF | VHGFG | HVF |
| VFQFL | GKIIH | KVGNY | VRGFS | KVF* |
| GFKFL | GKVIH | HVANW | LHGFS | KVF* |
| LFQFL | GKIIK | HVSNF | VKGFS | HVF* |
| VFRFL | GKIIK | KVGNF | VHGFA | KVF* |
| SFQFL | GKIIR | KVGQF | IHGFG | HVF* |
| VFQFL | GKIVH | KVANF | LHGFS | HVW* |
| VFNFL | GKIIR | RVGNF | VKGFS | RVF* |
| AFKFL | GKLIH | HVGNF† | IHGFG | HVY* |
| VFQFL | GKIIR | KVGNF | VKGFS | KVY* |
| VFNFL | GK†IIH | KVGNF | VHGFS | KVF* |
| AFQFL | GKIVH | H†VGNF | LHGFA | HVW* |

In the foregoing table, the same sequences are preferred where 1–5, 1–4, 1–3 or 1–2 amino acids have been deleted from the N-terminus. These specific compounds are also preferred.

Also preferred are compounds with the consensus sequence:(SEQ ID NO:36)

wherein X$_1$, B'$_3$, X$_4$, B$_7$, B$_{10}$, B$_{11}$, B*$_{17}$, and B$_{21}$ are as defined above.

Preferred among these are embodiments wherein:

X$_1$ is Ala, Leu or Val; or

B'$_3$ is Gln, His or Lys; or

X$_4$ is Leu or Phe; or

B$_7$ is Arg or Lys; or

B$_{10}$, B$_{11}$ and B$_{21}$ are His or Lys; or

B*$_{17}$ is His, Lys or modified Tyr, especially those wherein:

X$_1$ is Ala or Val; and

B'$_3$ is Gln, His or Lys; and

X$_4$ is Leu or Phe; and

B$_7$ is Arg or Lys; and

B$_{10}$, B$_{11}$ and B$_{21}$ are His or Lys; and

B*$_{17}$ is His, Lys or modified Tyr.

Among these more preferred forms, also, 1–5 amino may be deleted from the N-terminus. Particularly preferred are embodiments where 1–2 or 1–3 amino are thus deleted.

Particularly preferred forms of the compounds of the invention are Clavanins A, B C, D, and E, as well as the truncated forms shown below in comparison with Magainin 1 and Magainin 2.

| | | | | | |
|---|---|---|---|---|---|
| Magainin 1 SEQ ID NO:37 | - - - GI | GKFLH | SAGKF | GKAFV | GEI MKS |
| Magainin 2 SEQ ID NO:38 | - - - GI | GKFLK | SAGKF | GKAFV | NEI MKS |
| Clavanin A SEQ ID NO:39 | VFQFL | GKIIH | HVGNF | VHGFS | HVF* |
| Clavanin B SEQ ID NO:40 | VFQFL | GRIIH | HVGNF | VHGFS | HVF* |
| Clavanin C SEQ ID NO:41 | VFHLL | GKIIH | HVGNF | VY' GFS | HVF* |
| Clavanin D SEQ ID NO:42 | AFKLL | GRIIH | HVGNF | VY' GFS | HVF* |

| | | | | |
|---|---|---|---|---|
| Clavanin E<br>SEQ ID NO:43 | LFKLL | GKIIH | HVGNF | VHGFS HVF |
| Clavanin A<br>(3-23)<br>SEQ ID NO:39 | QFL | GKIIH | HVGNF | VHGFS HVF |
| Clavanin B<br>(3-23)<br>SEQ ID NO:40 | QFL | GRIIH | HVGNF | VHGFS HVF |
| Clavanin C<br>(3-23)<br>SEQ ID NO:41 | HLL | GKIIH | HVGNF | VY' GFS HVF |
| Clavanin D<br>(3-23)<br>SEQ ID NO:42 | KLL | GRIIH | HVGNF | VY' GFS HVF |

*indicates the amide form.

PREPARATION OF THE INVENTION COMPOUNDS

The invention compounds, often designated herein "clavanins" are essentially peptide backbones which may be modified at the N- or C-terminus and are linear peptides.

Standard methods of synthesis of peptides the size of clavanins are known. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by the gene and D-enantiomers can be employed in the synthesis. Thus, one very practical way to obtain the compounds of the invention is to employ these standard chemical synthesis techniques.

In addition to providing the peptide backbone, the N- and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

At the carboxy terminus, the carboxyl group may, of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. The carboxy terminus may also be esterified using alcohols of the formula ROH wherein R is hydrocarbyl (1–6C) as defined above. Similarly, the carboxy terminus may be amidated so as to have the formula —$CONH_2$, —CONHR, or —$CONR_2$, wherein each R is independently hydrocarbyl (1–6C) as herein defined. Techniques for esterification and amidation as well as neutralizing in the presence of base to form salts are all standard organic chemical techniques.

If the peptides of the invention are prepared under physiological conditions, the side-chain amino groups of the basic amino acids will be in the form of the relevant acid addition salts.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host.

Recombinantly produced forms of the clavanins may require subsequent derivatization to modify the N- and/or C-terminus.

For recombinant production, the DNA encoding the clavanins of the invention is included in an expression system which places these coding sequences under control of a suitable promoter and other control sequences compatible with an intended host cell. Types of host cells available span almost the entire range of the plant and animal kingdoms. Thus, the clavanins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-à-vis these infective agents.

The clavanins of the invention can be produced in a form that will result in their secretion from the host cell by fusing to the DNA encoding the clavanin, a DNA encoding a suitable signal peptide, or may be produced intracellularly. They may also be produced as fusion proteins with additional amino acid sequence which may or may not need to be subsequently removed prior to the use of these compounds as antimicrobials.

Thus, the clavanins of the invention can be produced in a variety of modalities including chemical synthesis and recombinant production or some combination of these techniques.

Any members of the clavanin class which occur naturally are supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 95% pure and more preferably more than 99% pure or is in a completely different context such as that of a pharmaceutical preparation.

ANTIBODIES

Antibodies to the clavanins of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The clavanins of the invention in immunogenic form are then injected into a suitable mammalian host and antibody titers in the serum are monitored.

Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies. The genes encoding monoclonal antibodies secreted by selected hybridomas or other cells may be recovered, manipulated if desired, for example, to provide multiple epitope specificity or to encode a single-chain form and may be engineered for expression in alternative host cells, such as CHO cells.

Thus, as used herein, "antibodies" also includes any immunologically reactive fragment of the immunoglobulins such as Fab, Fab' and F(ab')$_2$ fragments as well as modified immunoreactive forms such as Fv regions, which are produced by manipulation of the relevant genes (isolable, for example, from the appropriate hybridoma).

The antibodies of the invention are, of course, useful in immunoassays for determining the amount or presence of the clavanins. Such assays are essential in quality controlled production of compositions containing the clavanins of the invention. In addition, the antibodies can be used to assess the efficacy of recombinant production of the clavanins, as well as for screening expression libraries for the presence of clavanin encoding genes. They may also be used as affinity ligands for purifying and/or isolating the clavanins.

COMPOSITIONS CONTAINING THE CLAVANINS AND METHODS OF USE

The clavanins of the invention are effective in inactivating a wide range of microbial, including viral targets, including gram-positive and gram-negative bacteria, yeast, protozoa and certain strains of virus. Accordingly, they can be used in disinfectant compositions and as preservatives for materials such as foodstuffs, cosmetics, medicaments, or other materials containing nutrients for organisms. For use in such contexts, the clavanins are supplied either as a single clavanin, in admixture with several other clavanins, or in admixture with additional antimicrobial agents, especially protegrins. In general, as these are preservatives in this context, they are usually present in relatively low amounts, of less than 5%, by weight of the total composition, more preferably less than 1%, still more preferably less than 0.1%.

The peptides of the invention are also useful as standards in antimicrobial assays and in assays for determination of capability of test compounds to bind to endotoxins such as lipopolysaccharides.

For use as antimicrobials or antivirals for treatment of animal subjects, the clavanins of the invention can be formulated as pharmaceutical or veterinary compositions. Depending on the subject to be treated, the mode of administration, and the type of treatment desired—e.g., prevention, prophylaxis, therapy; the clavanins are formulated in ways consonant with these parameters. A summary of such techniques is found in Remington's *Pharmaceutical Sciences*, latest edition, Mack Publishing Co., Easton, Pa.

In general, for use in treatment or prophylaxis, the clavanins of the invention may be used alone or in combination with other antibiotics such as erythromycin, tetracycline, macrolides, for example azithromycin and the cephalosporins. Especially preferred is combination with one or more protegrins. Depending on the mode of administration, the clavanins will be formulated into suitable compositions to permit facile delivery to the affected areas. Use of the enantiomeric forms containing all D-amino acids may confer advantages such as resistance to those proteases, such as trypsin and chymotrypsin, to which the clavanins containing L-amino acids are less resistant.

The clavanins of the invention can be administered singly or as mixtures of several clavanins or in combination with other pharmaceutically active components, and in single or multiple administrations. The formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The clavanins can be administered also in liposomal compositions or as microemulsions.

If administration is to be oral, the clavanins of the invention must be protected from degradation in the stomach using a suitable enteric coating. This may be avoided to some extent by utilizing amino acids in the D-configuration, thus providing resistance to protease. However, the peptide is still susceptible to hydrolysis due to the acidic conditions of the stomach; thus, some degree of enteric coating may still be required.

As the examples will show, by appropriately choosing the member of the clavanin class of the invention, it is possible to adapt the antimicrobial activity to maximize its effectiveness with respect to a particular target microbe. As used herein, "microbe" will be used to include not only yeast, bacteria, and other unicellular organisms, but also viruses. The particular clavanin can also be chosen to be advantageous in a particular context, such as low salt or physiological salt, the presence or human serum, or conditions that mimic the conditions found in blood and tissue fluids.

Since certain forms of the clavanins are enhanced in effectiveness at reduced pH (i.e., those wherein histidine represents several of the basic residues, these forms can advantageously be used in low pH environments such as the stomach or sites of inflammation.

The clavanins of the invention may also be applied to plants or to their environment to prevent microbial-induced including viral diseases in these plants. Suitable compositions for this use will typically contain a diluent as well as a spreading agent or other ancillary agreements beneficial to the plant or to the environment.

Thus, the clavanins of the invention may be used in any context wherein an antimicrobial action is required. This use may be an entirely in vitro use, or the peptides may be administered to organisms.

In addition, the antimicrobial, including antiviral activity may be generated in situ by administering an expression system suitable for the production of the clavanins of the invention. Such expression systems can be supplied to plant and animal subjects using known techniques. For example, in animals, pox-based expression vectors can be used to generate the peptides in situ. Similarly, plant cells can be transformed with expression vectors and then regenerated into whole plants which are capable of their own production of the peptides.

The following examples are intended to illustrate but not to limit the invention.

EXAMPLE 1

Preparation of Clavanins A-D from *S. clava*

Tunics of *Styela clava* in batches of 50, obtained from Marinus Biologicals, Long Beach, Calif. were bathed briefly in absolute ethanol, blotted dry and transected peribasally over a 50 ml test tube that contained 0.25 g of disodium EDTA, into which the hemolymph was collected dripwise, and filtered through a fine sieve to remove components larger than hemocytes. $2 \times 10^8$ hemocytes were obtained and centrifuged (260×g, 5 min, 4° C.), resuspended in 50 ml of 0.34 M sucrose, recentrifuged and then extracted into ice cold 5% acetic acid, aided by brief sonication and overnight stirring at 4° C. The extract was centrifuged at 27,000×g for 30 min and the supernatants, which contained approximately 15 mg protein by BCA analysis, were removed for subsequent purification by the steps of ultrafiltration through a 10 kDa cutoff Amicon YM-10 membrane, followed by either gel permeation chromatography or (more usually) preparative electrophoresis, followed by reversed phase HPLC.

In more detail, the filtrates (≈3.5 mg of protein by BCA) were concentrated to 2 ml by vacuum centrifugation in a Speed Vac Concentrator (Savant Instruments, Hicksville, N.Y.). Gel permeation chromatography was performed on a 1.2×65 cm BioGel P-10 gel permeation column with 5% acetic acid. Preparative continuous acid-urea PAGE electrophoresis was performed as described by Harwig, S. S. L. et al., *Anal Biochem* (1993) 208:382. Active fractions were pooled and purified by RP-HPLC a 4.6×250 mm Vydac C18 column, using various linear gradients of acetonitrile in 0.1% trifluoroacetic acid (TFA) or 0.13% heptafluorobutyric acid (HFBA). Throughout this multistep procedure, fractions were lyophilized, concentrated and tested for antimicrobial activity against *Listeria monocytogenes* strain EGD by a radial diffusion technique described in Lehrer, R. I. et al., *J Immunol Methods* (1991) 137:167. In these assays, the underlay gels contained 9 mM sodium phosphate and 1 mM sodium citrate buffer, 0.30 mg/ml of trypticase soy broth powder (BBL, Cockeysville, Md.) and 1% agarose at a final pH of 6.5.

FIG. 1 shows the results of final purification on HPLC. As shown in FIG. 1, initial separation provided peaks a and b which were then rechromatographed to separate peak a into Clavanins A and B and peak b into Clavanins C and D. Neither Clavanin A nor Clavanin B showed significant absorbency at 280 nm although Clavanins C and D both showed such absorbency.

Amino acid compositions were determined for Clavanins A and B; the hydrolysis of Clavanins C and D showed an unknown peak that emerged before phenylthiocarbamyl (PTC) tyrosine, suggesting the presence of one or more modified or unusual amino acid residues, although the retention time of this peak did not match either PTC-methyl lysine or PTC-methyl histidine.

As shown below, the complete amino acid sequences of Clavanins A–D were determined in part by gas-phase Edman degradation with a Portion Model 2090 instrument using 300 pmole samples. Y' indicates a modified tyrosine residue, in this case, o-methyl tyrosine. The * indicates amidation.

| | | | | | |
|---|---|---|---|---|---|
| Clavanin A SEQ ID NO:39 | VFQFL | GKIIH | HVGNF | VHGFS | HVF* |
| Clavanin B SEQ ID NO:40 | VFQFL | GRIIH | HVGNF | VHGFS | HVF* |
| Clavanin C SEQ ID NO:41 | VFHLL | GKIIH | HVGNF | VY' GFS | HVF* |
| Clavanin D SEQ ID NO:42 | AFKLL | GRIIH | HVGNF | VY' GFS | HVF* |

Nineteen of the 22 residues of Clavanins C and D could be identified by direct peptide sequencing as indicated above. The remaining residues, $Tyr_{17}$, $His_{21}$, $Val_{22}$ and $Phe_{23}$ were identified by 3' RACE-PCR cloning of a precursor having the partial sequence HHVGNFVYGFSHVF(G). The masses for Clavanins C and D as determined by FAB-MS were 14 mass units less than their measured values, suggesting that one residue was methylated. Because no unmodified tyrosine was found in the amino acid analysis, the methylated residue appears to be $Tyr_{17}$. The presence and position of the parenthesized glycine residue in the precursor suggests that Clavanins C and D are amidated. This is consistent with the amidation of Clavanins A and B set forth below.

Two forms of synthetic Clavanin A were prepared, one as the free acid at the C-terminus and the other in C-terminal amidated form. These were synthesized by SynPep, Dublin, Calif., using F-moc chemistry. The electrospray massav values for the acid form were 2667.2 (expected 2667.1) and for the amide 2664.6 (expected 2666.1) and the peptides were purified to apparent homogeneity by reverse-phase HPLC. By comparing migration values by AU PAGE, it was concluded that both Clavanin A and Clavanin B contained C-terminal amidation.

Mass values for the clavanins are as follows:

Clavanin A: 2667.1;
Clavanin B: 2694.8;
Clavanin C: 2682.1;
Clavanin D: 2673.0.

EXAMPLE 2

Characterization of Conformation

The circular dichroism spectrum for synthetic Clavanin A was determined on an Aviv Model 62DS Spectral Polarimeter (Aviv Associates, Lakewood, N.J.) in 80% TFA at 25° C. using a rectangular cell with a 0.5 mm path length. Similar measurements were made using synthetic Clavanin A contained in large (≈100 nm) unilamellar liposomes of simulated *S. aureus* lipids contained in a 3:1 molar ratio of egg phosphatidyl glycerol and cardiolipin, prepared by an extrusion technique using a LiposoFast device (Avestin, Ottawa, Canada). The results are shown in FIG. 2 for the synthetic form and show a characteristic α-helical conformation with a double minimum at ≈208 and ≈222 nm. Similarly determined spectra of native Clavanin A displayed maxima at ≈210 and ≈224 nm. FIG. 2 also shows a helical wheel projection of Clavanin A indicating an amphipathic helix with spatial segregation of the hydrophobic and charged residues.

EXAMPLE 3

Recovery of Clavanin-Encoding cDNA

Total RNA from tunicate pharyngeal tissues was isolated and purified using a total RNA separator kit (Clontech, Palo Alto, Calif.). First strand cDNA synthesis and clavanin 3' side cDNA amplification were carried out with a 3'RACE kit (Gibco BRL, Gaithersburg, Md.) using 1 μg of total pharyngeal RNA, and 10 μM adapter primer to obtain the first strand of cDNA. A degenerate 30-base primer, 5'-GTCGACTAGTCAYCAYGTIGGIAAYTTYGT-3'(SEQ ID NO:44), where Y represents T or C, I represents inosine, and the singleunderlining indicates a Spe I restriction site that corresponded to amino acids 11–17 of clavanins A, B, C, and D (His-His-Val-Gly-Asn-Phe-Val) (SEQ ID NO:45) was designed.

PCR was performed in a total volume of 50 μl that contained: 1/10 vol. of first strand cDNA, 10 pmol each of degenerate primer and AUAP primer, and 5 U of pfu DNA polymerase. The reaction was run for 35 cycles, with 1 min denaturation (94° C.), 1 min annealing (48° C.), and 2.5 min extension (72° C.) per cycle. PCR product about 250 bp in size was cloned into pCRScript SK vector (Stratagene, La Jolla, Calif.). DNA sequencing results confirmed that it was the 3' side cDNA sequence of clavanin.

To obtain a DNA library, pharyngeal tissues (the functional equivalent of bone marrow in tunicates) were removed from live *Styela clava* and stored at −70° C. A custom cDNA library was constructed for us in λTripIEx™ by Clontech Laboratories. *E. coli* stain XL1-Blue was used as a host, and phage plaques DNA was transferred to nylon membranes (Dupont, Boston, Mass.). The filters were hybridized with $^{32}$P-labeled 250 bp clavanin 3' side cDNA, as per the above. Hybridization was carried out at 50° C. overnight with Rapid-hyb buffer (Amersham). The filters were washed several times, finally at 60° C. in 0.1×SSC and 0.1% SDS, and exposed to S-ray film with an intensifying screen at −70° C. Positive clones were subjected to one or two additional rounds of plaque screening at low density. Finally, 50 positive clones were identified from approximately $1.2 \times 10^5$ clones.

To obtain DNA sequence, λ phage DNA was purified using a Lamda kit (AIAGEN, Chatsworth, Calif.). The purified DNA or picked plaques were subjected to long-distance PCR using LD-Insert Screening Amplimers (Clontech Lab., Palo Alto, Calif.). PCR amplification was performed according to the manufacturer's protocol. The PCR products of inserts were purified from low melting agarose gel, and sequenced directly by fluoresceinlabeled dideoxynucleotide terminator method, and the sequencing reaction were analyzed on an Applied Biosystems 373 DNA Sequencer (Perkin-Elmer, Palo Alto, Calif.). Of the eight clones sequenced to date, we have found 2 clavanin A, 4 clavanin D, 1 clavanin D, and 1 clavanin E. The sequence of each precursor is shown in FIGS. 3A–3E.

The 5'-cDNA inserts contain a short untranslated part (≈20 bp). As shown from the sequence information, clavanins are synthesized as prepropetides with a typical, ≈18–20 residue-long signal sequence followed by a short anionic propiece (SL)(EERKSEEEK(SEQ ID NO:46)). A glycine residue follows the amino acids present in the mature clavanins, as expected for amidated peptides. Finally, there are 27 amino acids that follow the mature clavanin+glycine sequence. (See FIG. 3E)

Thus, the clavanins are encoded as C-terminal extended proclavanins; post-translational processing removes the C-terminal 27 amino acids and amidates the residual peptide chain.

EXAMPLE 4

Antimicrobial Activity of the Clavanins

In initial experiments, the antimicrobial activity of Clavanin A was compared with that of the known antimicrobial peptides Magainin 1 and Cecropin P1 against *Listeria monocytogenes* and *E. coli* by a classical colony counting technique. The peptides were mixed with midlogarithmic phase bacteria in a sterile solution of 10 mM sodium phosphate buffer, pH 6.5 containing 0.3 mg/ml of trypticase soy broth powder. Approximately 50–100 μl of the mixtures were incubated in a 37° C. shaking water bath and 10 μl aliquots removed at intervals and either plated directly or diluted with a Spiral Plater (Spiral Systems Instruments, Bethesda, Md.) as described by Gilchrist, J. E. et al., *J Assoc Off Anal Chem* (1977) 60:807. The colonies were counted after overnight incubation.

Figure 4:
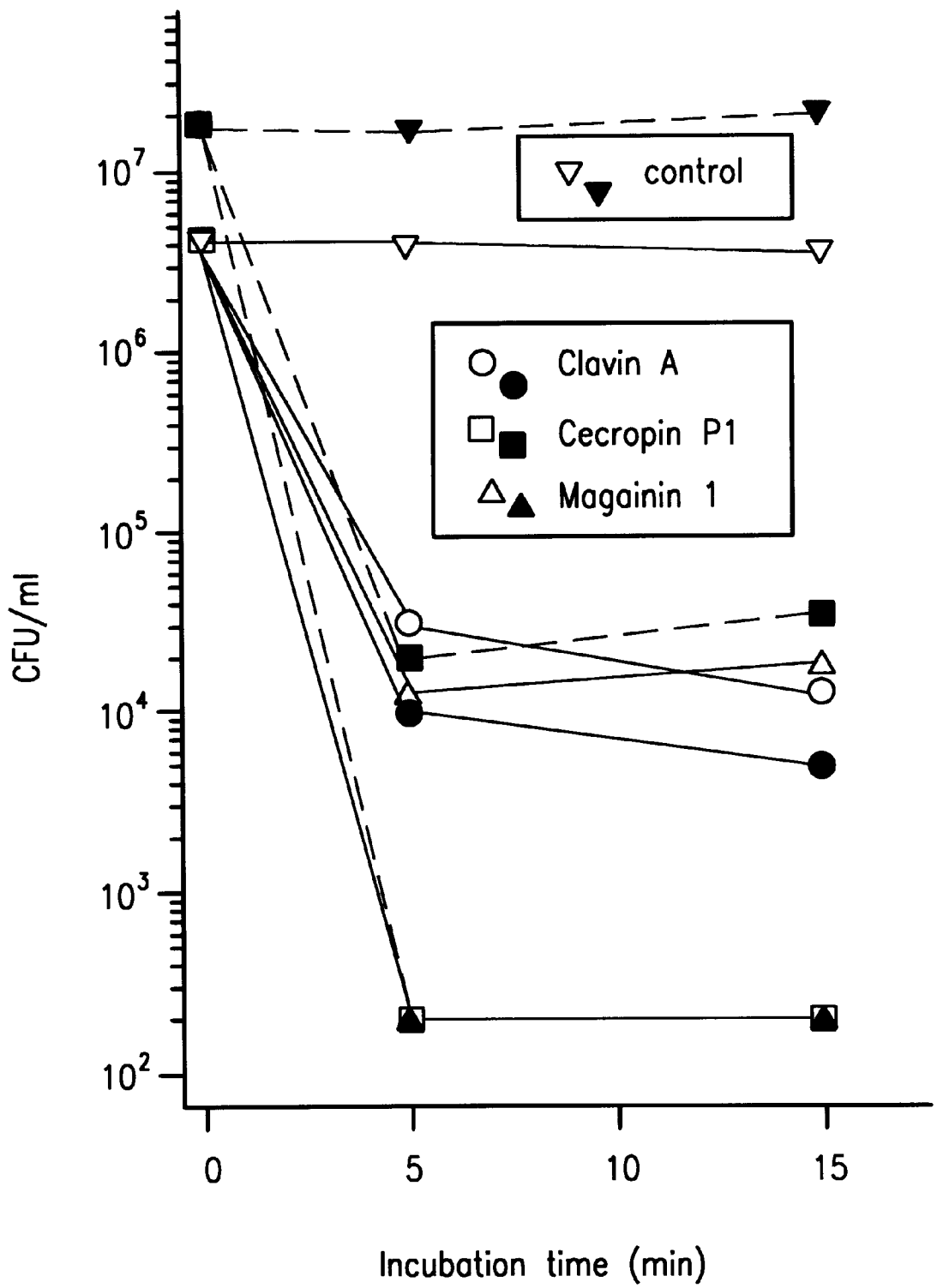
FIG. 4 shows a graphic representation of antimicrobial activity of Clavanin A against *E. coli* and *L. monocytogenes* as compared to the activity of Cecropin P1 and Magainin 1.

The results are shown in FIG. 4.

All of the peptides, provided at low concentrations, killed these bacteria within 5 min. Clavanin A and Magainin 1 at 1.6 μg/ml showed identical activity against *E. coli* ML-35P, reducing the colony count by more than 2 log units; at 3.5 μg/ml Clavanin A caused a rapid more-than-3 log unit reduction in *L. monocytogenes* CFU, an effect that was intermediate between that of Cecropin P1 and that of Magainin 1.

Figure 5C:
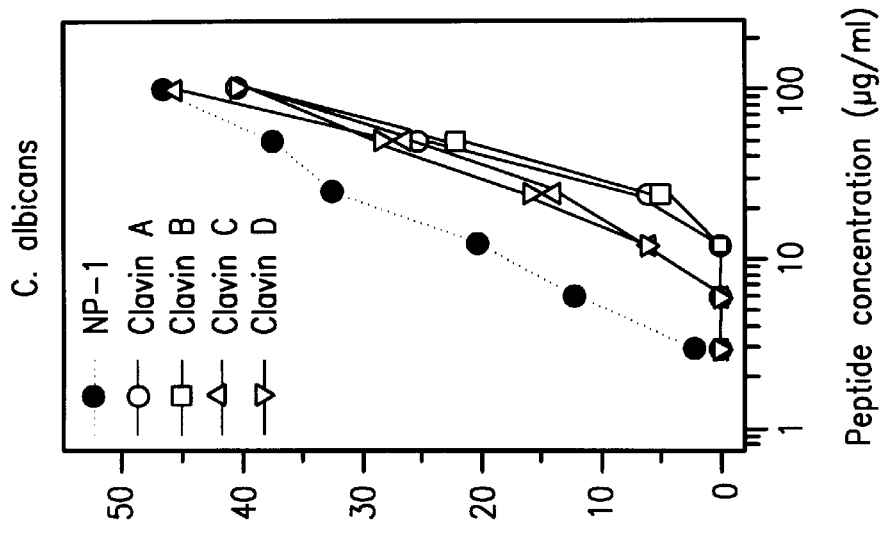
FIG. 5 shows comparative antimicrobial activity of Clavanins A, B, C and D with respect to *E. coli, L. monocytogenes* and *C. albicans*.
Figure 5B:
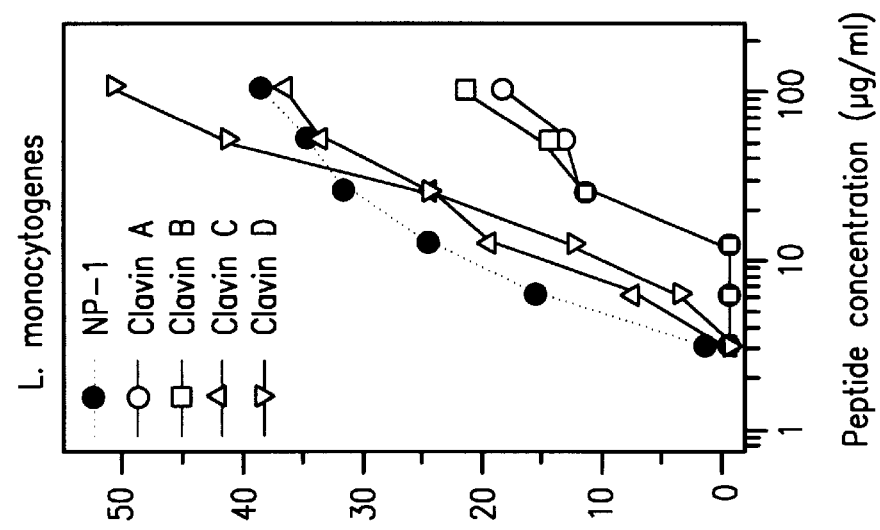
Figure 5A:
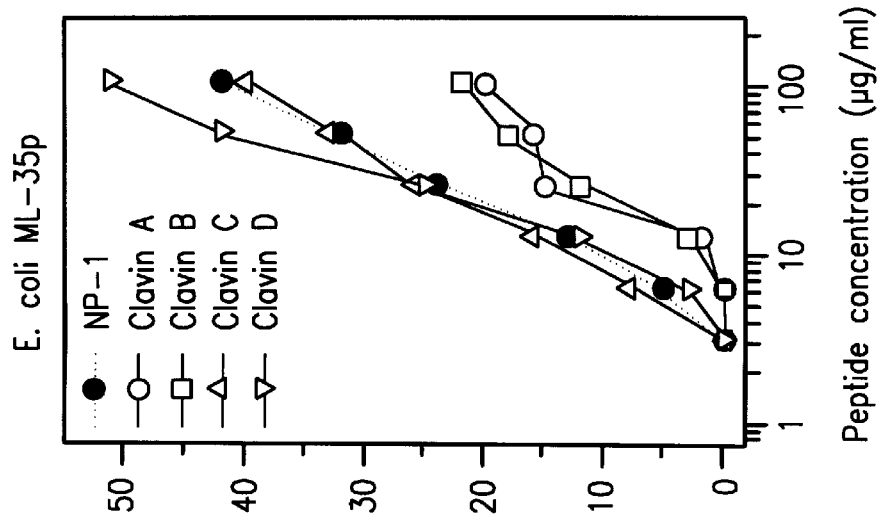

FIG. 5 shows the results of antimicrobial assays conducted using a more sensitive radial diffusion method of Lehrer et al. (supra) against *E. coli* ML-35P, *L. monocytogenes* Strain EGD and yeast phase *C. albicans*. Clavanins C and D were approximately 3–5-fold more potent than A and B with respect to the bacterial assays although similar results were obtained against *C. albicans*.

In addition to Cecropin P1 and Magainin 1, the activity of Clavanin A(K) was also tested. Clavanin A(K) is identical to Clavanin A except that all of the histidine residues are replaced by lysine. Table 1 shows a summary of the comparative activities of the peptide Cecropin P1, Magainin 1, Clavanin A and Clavanin A(K) versus a number of Gram-positive and Gram-negative bacteria. The data are provided as minimal bacteriocidal concentrations expressed in μg/ml which are the X-intercepts of radial diffusion assays performed at pH 6.5 in an underlay that contained 10 mM buffer (9:1 citrate:phosphate), 1% agarose and 0.3 mg trypticase soy powder/ml.

| Organism: | Cecropin P1 | Magainin 1 | Clavanin A | Clavanin A(K) |
|---|---|---|---|---|
| Gram-positive | | | | |
| S. aureus 930918-3 | >200 | >200 | >200 | 6.8 |
| MRSA 30371 | >200 | >200 | 6.7 | 5.6 |
| MRSA 28841 | >200 | >200 | 1.4 | 2.5 |
| E. faecalis CDC 21 (VR) | >200 | >200 | 1.7 | 6.5 |
| E. faecium 94.132 (VR) | 7.5 | 5.5 | 0.14 | 0.36 |
| E. faecium | 6.5 | 7.3 | 0.77* | 0.67 |
| L. monocytogenes EGD | 6.0 | 7.0 | 0.39 | 0.41 |
| Gram-negative | | | | |
| E. coli ML-35p | 0.64 | 1.2 | 5.0 | 2.2 |
| E. coli mcr 106 | 0.54 | 0.92 | 1.7 | 0.66 |
| E. coli BAS 894 | 0.41 | 1.3 | 0.17* | 0.46 |
| S. typhimurium 14028s | 0.72 | 2.7 | >200 | 1.9 |
| S. typhimurium 7953s | 0.43 | 1.1 | 0.22* | 1.2 |
| K. pneumoniae 2270 | 0.70 | 1.2 | >200 | 1.3 |
| P. aeruginosa SBI-N | 0.44 | 0.31 | 0.19* | 0.60 |

-continued

| Organism: | Cecropin P1 | Magainin 1 | Clavanin A | Clavanin A(K) |
|---|---|---|---|---|
| P. aeruginosa MR 2133 | 0.51 | 0.44 | 0.29* | 0.91 |
| P. aeruginosa MR 3007 | 0.71 | 0.93 | 0.17* | 0.42 |

As shown, the clavanins are considerably more effective against certain Gram-positive bacteria than are Cecropin P1 or Magainin 1; all of the peptides, nevertheless, have wide-spectrum antimicrobial activity.

EXAMPLE 5

Effect of pH on Antimicrobial Activity

The effect of pH on antimicrobial activity against several organisms was tested in a pH range wherein histidine becomes comparably charged to lysine. FIGS. 6–8 show the results for native or synthetic Clavanin A and synthetic Clavanin A(K) using defensin NP-2 as a control, with respect to L. monocytogenes, E. coli, and C. albicans respectively. The radial diffusion assays were conducted as described in Examples 1 and 3 above. As shown in FIG. 6, the pH of the assay has no effect on the activity of defensin NP-2, but both native Clavanin A and synthetic Clavanin A are relatively inactive at pH 7.5 although they are highly antimicrobial at pH 5.5–6.5. Synthetic Clavanin A(K) is comparably active at all three pHs. Similar results are obtained as shown in FIGS. 7 and 8 for E. coli and C. albicans.

EXAMPLE 6

Effect of Other Parameters

A comparison of the antimicrobial activity of synthetic Clavanin A in the amide and free-acid form against L. monocytogenes and E. coli showed that both behaved similarly with respect to both bacteria.

When the radial diffusion assays were run adding 100 mM NaCl to the underlay gels, the presence of the salt appeared to diminish but not to destroy the activity of the synthetic Clavanin A peptide with respect to L. monocytogenes and E. coil.

Figure 10A:
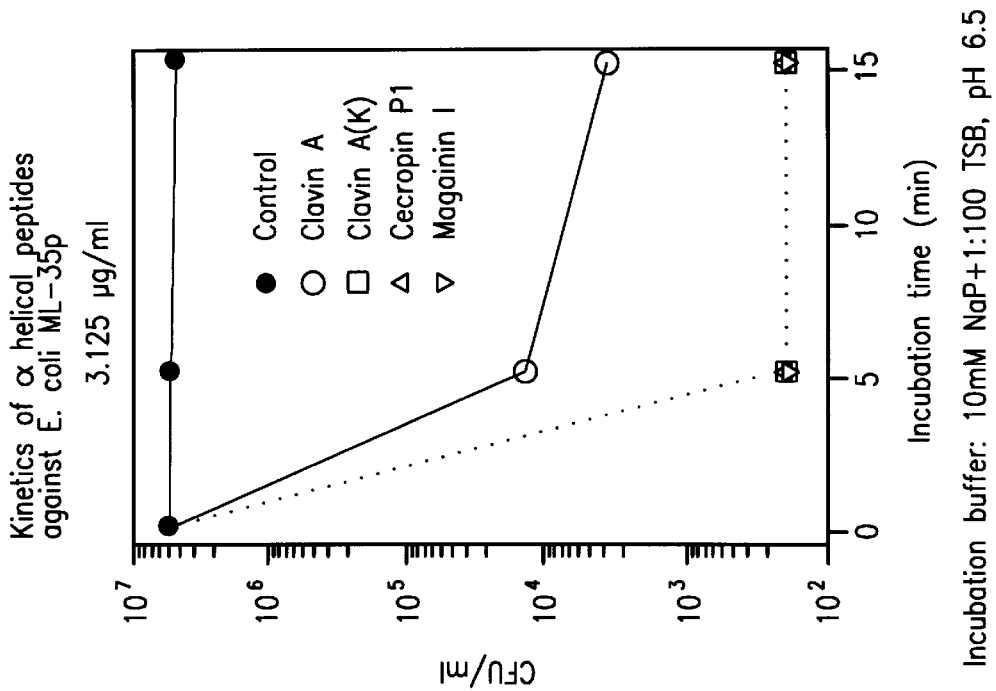
FIG. 10 shows the kinetics of Clavanin A, Clavanin A(K) and comparatively, Cecropin P1 and Magainin 1 in their antimicrobial action against *E. coli* ML-35P.
Figure 10B:
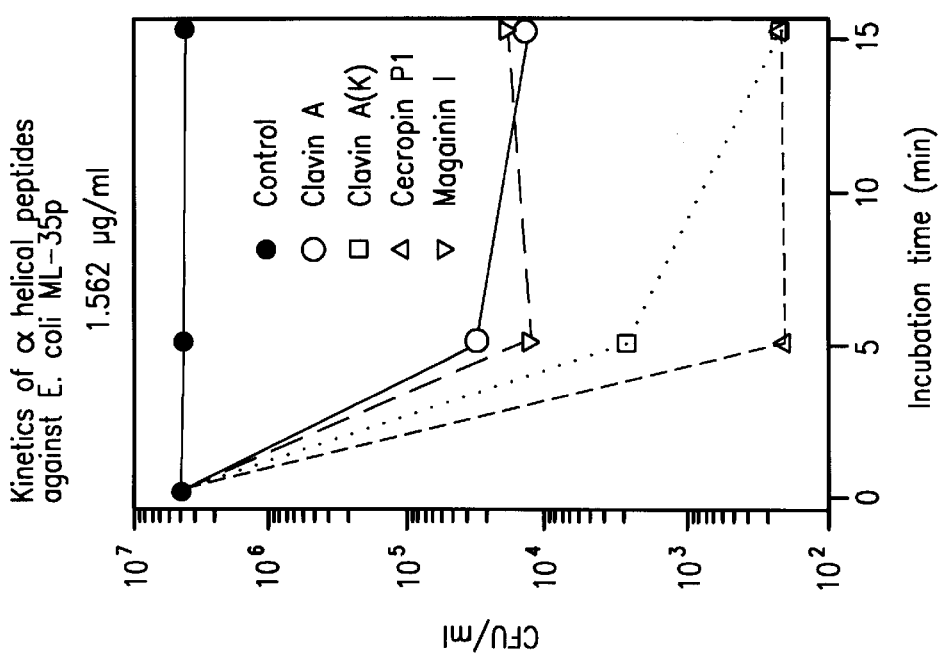

The kinetics of the antimicrobial activity of Clavanin A and Clavanin A(K) were also tested in a colony count assay using 10 mM sodium phosphate plus 1:100 TSB buffer at pH 6.5. Mid log phase L. monocytogenes were incubated with 3.5 or 7.0 μg/ml of the test peptides and samples were removed after 5 and 15 min; concentrations with respect to E. coli were 1.5 or 3.1 μg/ml. The results of these experiments are shown in FIG. 9 and 10. Both Clavanin A and Clavanin A(K) have an antimicrobial effect after as little as 5 min. at these concentrations.

EXAMPLE 7

Truncated Forms

Two truncated forms of Clavanin E were prepared—one wherein two amino acids were deleted from the N-terminus (Clavanin E(3-23)) and one wherein five amino acids were deleted from the N-terminus (Clavanin E(6-23)). Thus, the amino acid sequences of these peptides are:

| E(3-23) of SEQ ID NO:43) | KLL | GKIIH | HVGNF | VHGFS | HVF* |
|---|---|---|---|---|---|
| E(6-23) of SEQ ID NO:43) | | GKIIH | HVGNF | VHGFS | HVF* |

Clavanin E(2-23) was tested in the standard underlay assay described in Example 1 herein wherein the underlay contained 10 mM sodium phosphate buffer, pH 7.4 and 1:100 trypticase soy broth with and without 200 mM NaCl. The known antimicrobials cecropin A, cecropin B, and cecropin P1 were used as controls.

Against Group B Streptococcus, E(3-23) was slightly more active than any of the cecropins without salt present, and dramatically more so in the presence of salt, as the activity of cecropins against this organism is drastically diminished in the presence of this salt concentration.

Against L. monocytogenes, again Clavanin E(3-23) was more active than any of the cecropin controls and maintained activity in the presence of 100 mM salt better than any of these, although the effect of salt on the cecropins in this organism is not as great.

Against S. aureus, again, E(3-23) appeared more slightly more active than the cecropins in the presence of salt and dramatically more active when 200 mM salt was present as the activity of the cecropins at this salt concentration was destroyed.

With respect to E. coli ML-35P, the cecropins and E(3-23) appeared comparably active; the presence of 100 mM sodium chloride did not appear measurably to effect the activity of any of these antimicrobials.

Against P. aeruginosa, again, E(3-23) was comparably active to the cecropins in both the presence and absence of 100 mM salt although cecropin P-1 and A were slightly more active than E(3-23).

Against Burkaholderia cepacia, the presence of 200 mM sodium chloride did not affect measurably the activity of any of the cecropins and only slightly diminished the activity of E(3-23).

The foregoing results are summarized in FIGS. 11A–11F.

Figure 12B:
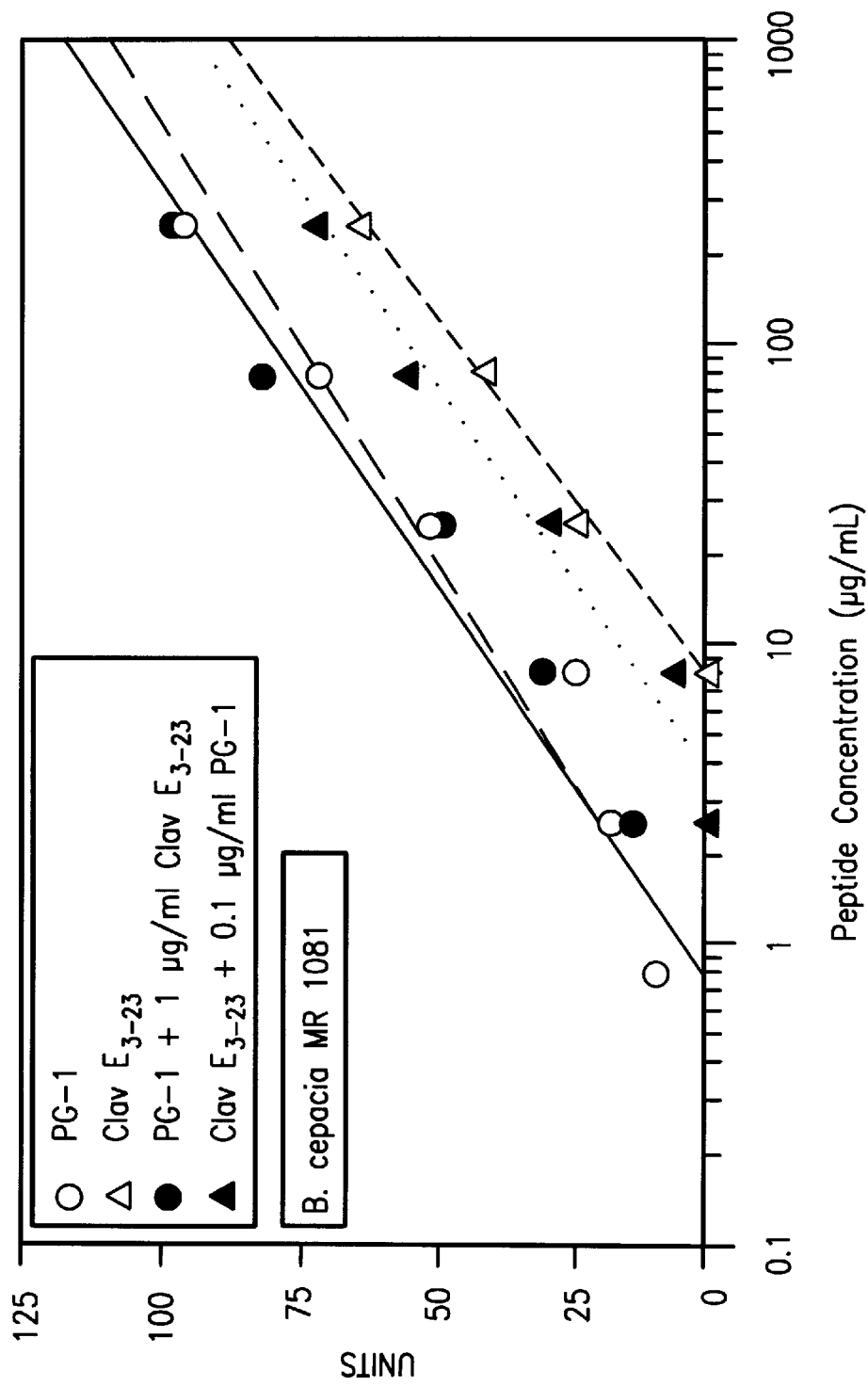
Figure 12C:
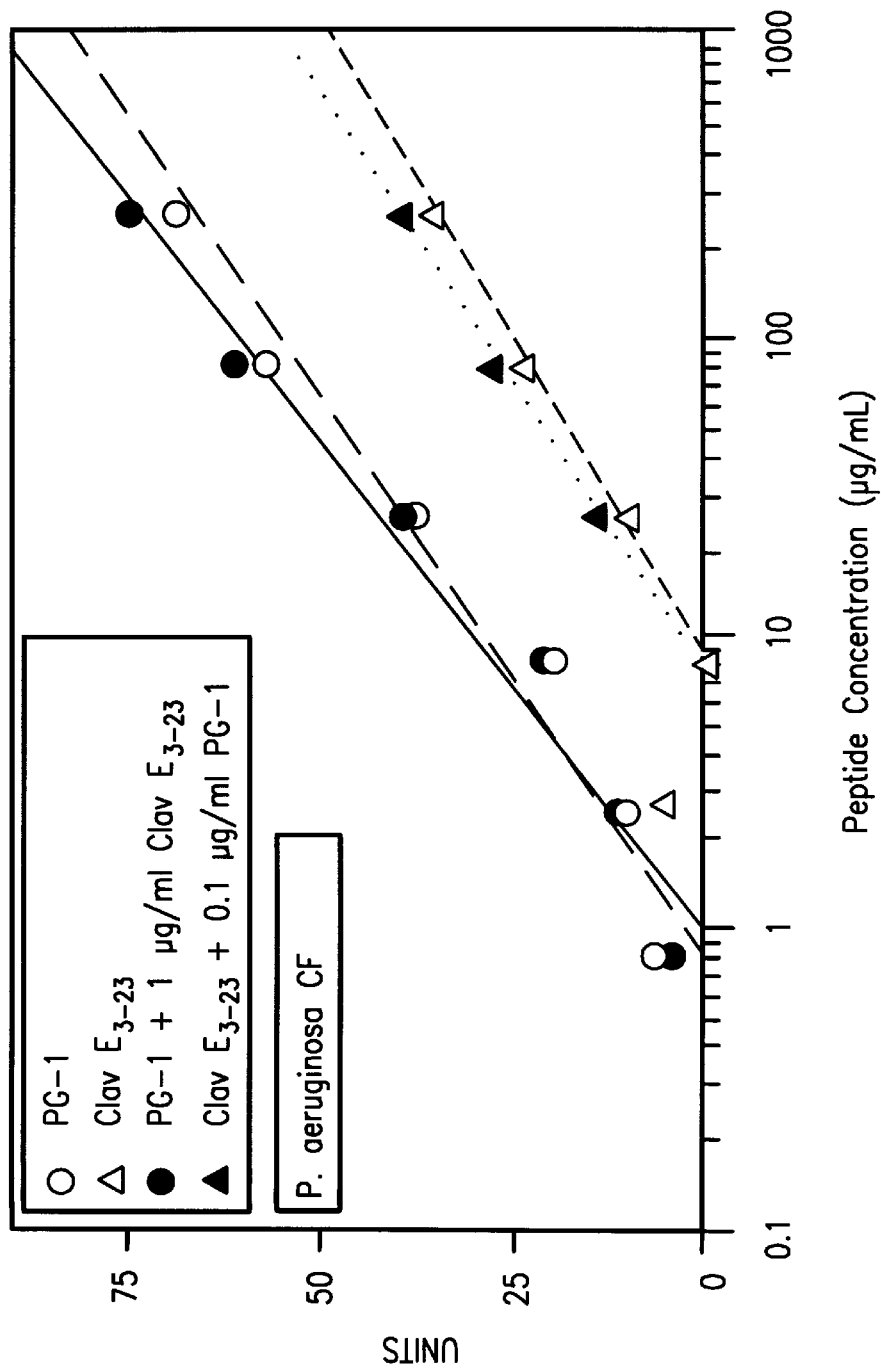

The standard underlay assay was again conducted supplying both E(3-23) and PG-1 to the underlay. A synergistic effect of these two antimicrobials against microorganisms is obtained as shown in FIGS. 12A–12C. In these assays, the underlay contained in addition to 1% agarose, 10 mM sodium phosphate buffer, pH 7.4, 1:100 trypticase soy broth and 200 mM NaCl. The underlays contain PG-1 alone, E(3-23) alone, or combinations of E(3-23) and PG-1.

As shown in FIG. 12A, when the test organism was S. aureus, in the absence of E(3-23) the minimum bacterial concentration (MBC) of PG-1 was approximately 0.9 μg/ml (x intercept), but when 4 μg/ml of E(3-23) was present, the MBC for PG-1 was 0.07 μg/ml. Similarly, in the absence of PG-1, the MBC of E(3-23) was 7.5 μg/ml in the presence of 0.5 μg/ml PG-1, it was 2.5 μg/ml.

FIG. 12B shows the results with respect to B. cepacia. Incorporation of 0.1 mg/ml PG-1 decreased MBC of E(3-23) from 7.5 μg/ml to 2.5 μg/ml; the presence of 1 μg/ml E(3-23) did not effect MBC for PG-1. Similarly, as shown in FIG. 12C, when P. aeruginosa was the test organism, neither synergy nor antagonism was shown.

Finally, the activity of Clavanins A and E as well as E(3-23) and E(6-23) was tested against various target organisms at two pHs with and without salt. As shown in FIG.

13A, all of the Clavanins are comparably effective with respect to each other against *E. coli, L. monocytogenes, P. aeruginosa, S. areus* and *C. albicans*. However, the presence of 200 mM sodium chloride at pH 5.5 (FIG. 13B) essentially destroyed the activity of E(6-23) and lowered the activity of Clavanin A with respect to most organisms. Clavanin E maintained its activity against *S. aureus*, however and the activity of E and E(3-23) was better maintained than that with respect to Clavanin A. In all cases, activity against *C. albicans* was greatly diminished.

At pH 7.4, in the absence of salt, both E(3-23) and E(6-23) were greatly more active against most of the test organisms as compared to E or A. Only E(3-23) was measurably active against *C. albicans*. This is shown in FIG. 14A. FIG. 14B shows the results in the presence of 200 mM NaCl where E(3-23) was the only antibiotic to maintain its bacteriocidal activity; none of the peptides were active against *C. albicans* under these conditions.

The Tables below show the minimal bacteriocidal concentrations of PG-1, histatin 5, and Clavanin E(3-23) against various organisms under various conditions. E(3-23) was active over a broad pH range and, unlike hisatin 5, it retained activity in the presence of physiological sodium chloride concentrations.

Low salt conditions (10 mM phosphate)

|  | pH 74 | | | pH 5.5 | | |
| --- | --- | --- | --- | --- | --- | --- |
|  | PG-1 | Hs-5 | E(3-23) | PG-1 | Hs-5 | E(3-23) |
| *E. coli* | 0.04 | 2.6 | 0.9 | 0.05 | 1.1 | 0.6 |
| *P. aeruginosa* | 0.40 | 1.4 | 2.5 | 0.20 | 2.2 | 0.8 |
| *L. monocytogenes* | 0.09 | 9.2 | 1.2 | 0.10 | 11.8 | 0.6 |
| *C. albicans* | 0.20 | >250 | >80 | 0.06 | 7.2 | 3.7 |

High salt conditions (10 mM phosphate+100 mM NaCl)

|  | pH 74 | | | pH 5.5 | | |
| --- | --- | --- | --- | --- | --- | --- |
|  | PG-1 | Hs-5 | E(3-23) | PG-1 | Hs-5 | E(3-23) |
| *E. coli* | 0.20 | >250 | 1.2 | 0.04 | 60.6 | 3.6 |
| *P. aeruginosa* | 0.40 | >250 | 2.5 | 0.20 | >500 | 1.1 |
| *L. monocytogenes* | 0.20 | >250 | 1.2 | 0.10 | >500 | 1.2 |
| *C. albicans* | 1.60 | >250 | >80 | 0.10 | >500 | >250 |

We claim:

1. A compound in isolated form of the formula

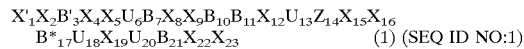 (1) (SEQ ID NO:1)

including the salts, esters, amides, and acylated forms thereof, said compound having antimicrobial activity and an α-helical conformation, wherein X is a hydrophobic amino acid residue selected from the group consisting of Tyr, Val, Ile, Leu, Met, Phe, and Trp;

X' is a small or a hydrophobic amino acid residue selected from the group consisting of Gly, Ser, Ala, Thr, Tyr, Val, Ile, Leu, Met, Phe, and Trp;

B is a basic amino acid residue selected from the group consisting of Arg, Lys, and His;

B' is a basic or a polar/large amino acid residue selected from the a group consisting of Arg, Lys, His, Asn, and Gln;

B* is a basic or a hydrophobic amino acid residue selected from the group consisting of Arg, Lys, His, Tyr, Val, Ile, Leu, Met, Phe, and Trp;

U is a small amino acid residue selected from the group consisting of Gly, Ser, Ala, and Thr;

Z is a polar/large amino acid residue selected from the group consisting of Asn and Gln; and wherein one or more $X'_1 X_2 B'_3 X_4 X_5$ may be truncated.

2. The compound of claim 1 wherein at least one amino acid residue is in the D configuration.

3. The compound of claim 1 wherein at least one bond between two amino acid residues is a peptide bond mimic.

4. The compound of claim 1, wherein $X'_1$ is Val, Leu, Ile, or Ala; or $X_2$ is Phe, Trp or Tyr; or $X_4$ and $X_5$ is each independently selected from the group consisting of Phe, Leu, Tyr, and Val; or $U_6$ is Gly, Ser or Ala; or $B_7$ is Lys or Arg; or $X_8$ and $X_9$ is each independently selected from the group consisting of Ile, Leu and Val; or $X_{12}$ is Val, Ile, or Leu; or $U_{13}$ is Ala, Ser or Gly; or $X_{15}$ and $X_{16}$ is each independently selected from the group consisting of Phe, Tyr, Trp, Val, Leu and Ile; or $B*_{17}$ is His, Lys, Arg, Trp, Phe or Tyr;

$U_{18}$ is Ala, Ser or Gly; or $X_{19}$ is Phe, Tyr or Trp; or $U_{20}$ is Gly, Ala or Ser; or each of $X_{22}$ and $X_{23}$ is Ile, Val, Leu, Phe, Tyr or Trp.

5. The compound of claim 1 wherein $X'_1$ is Val, Leu, Ile, or Ala; and $X_2$ is Phe, Trp or Tyr; and $X_4$ and $X_5$ is each independently selected from the group consisting of Phe, Leu, Tyr, and Val; and $U_6$ is Gly, Ser or Ala; and $B_7$ is Lys or Arg; and $X_8$ and $X_9$ is each independently selected from the group consisting of Ile, Leu and Val; and $X_{12}$ is Val, Ile, or Leu; and $U_{13}$ is Ala, Ser or Gly; and $X_{15}$ and $X_{16}$ is each independently selected from the group consisting of Phe, Tyr, Trp, Val, Leu and Ile; and $B*_{17}$ is His, Lys, Arg, Trp, Phe or Tyr;

$U_{18}$ is Ala, Ser or Gly; and $X_{19}$ is Phe, Tyr or Trp; and $U_{20}$ is Gly, Ala or Ser; and each of $X_{22}$ and $X_{23}$ is Ile, Val, Leu, Phe, Tyr or Trp.

6. The compound of claim 1 wherein $X_2$ is Phe; or $X_5$ is Leu; or $U_6$ is Gly; or $B_7$ is Arg or Lys; or $X_8$ and $X_9$ are Ile; or $B_{10}$ and $B_{11}$ are His or Lys; or $X_{12}$ is Val; or $U_{13}$ is Gly; or $Z_{14}$ is Asn; or $X_{15}$ is Phe; or $X_{16}$ is Val; or $U_{18}$ is Gly; or $X_{19}$ is Phe; or $U_{20}$ is Ser; or $B_{21}$ is His or Lys; or $X_{22}$ is Val; or $X_{23}$ is Phe.

7. The compound of claim 1 wherein $X_2$ is Phe; and $X_5$ is Leu; and $U_6$ is Gly; and $B_7$ is Arg or Lys; and
$X_8$ and $X_9$ are Ile; and
$B_{10}$ and $B_{11}$ are His or Lys; and
$X_{12}$ is Val; and
$U_{13}$ is Gly; and
$Z_{14}$ is Asn; and
$X_{15}$ is Phe; and
$X_{16}$ is Val; and
$U_{18}$ is Gly; and
$X_{19}$ is Phe; and
$U_{20}$ is Ser; and
$B_{21}$ is His or Lys; and
$X_{22}$ is Val; and
$X_{23}$ is Phe.

8. The compound of claim 4 wherein
$X_1$ is Val, Leu or Ala;
$B'_3$ is Gln, His or Lys;
$X_4$ is Phe or Leu; or
$B^*_{17}$ is His, Lys or modified Tyr.

9. The compound of claim 7 wherein
$X_1$ is Val, Leu or Ala;
$B'_3$ is Gln, His or Lys;
$X_4$ is Phe or Leu; or
$B^*_{17}$ is His, Lys or modified Tyr.

10. A compound in isolated form of the formula:

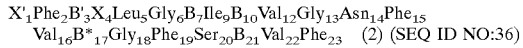
$X'_1 Phe_2 B'_3 X_4 Leu_5 Gly_6 B_7 Ile_9 B_{10} Val_{12} Gly_{13} Asn_{14} Phe_{15} Val_{16} B^*_{17} Gly_{18} Phe_{19} Ser_{20} B_{21} Val_{22} Phe_{23}$ (2) (SEQ ID NO:36)

including the salts, esters, amides, and acylated forms thereof,
said compound having antimicrobial activity and an α-helical conformation,
wherein X is a hydrophobic amino acid residue selected from the group consisting of Tyr, Val, Ile, Leu, Met, Phe, and Trp;
X' is a small or a hydrophobic amino acid residue selected from the group consisting of Gly, Ser, Ala, Thr, Tyr, Val, Ile, Leu, Met, Phe, and Trp;
B is a basic amino acid residue selected from the group consisting of Ara, Lys, and His;
B' is a basic or a polar/large amino acid residue selected from the group consisting of Ara, Lys, His, Asn, and Gln;
B* is a basic or a hydrophobic amino acid residue selected from the group consisting of Arg, Lys, His, Tyr, Val, Ile, Leu, Met, Phe, and Trp; and
wherein $X'_1$ may be truncated.

11. The compound of claim 10 wherein
$X_1$ is Ala, Leu or Val; or
$B'_3$ is Gln, His or Lys; or
$X_4$ is Leu or Phe; or
$B_7$ is Arg or Lys; or
$B_{10}$, $B_{11}$ and $B_{21}$ are His or Lys; or
$B^*_{17}$ is His, Lys or Tyr.

12. The compound of claim 10 wherein
$X_1$ is Ala, Leu or Val; and
$B'_3$ is Gln, His or Lys; and
$X_4$ is Leu or Phe; and
$B_7$ is Arg or Lys; and
$B_{10}$, $B_{11}$ and $B_{21}$ are His or Lys; and
$B^*_{17}$ is His, Lys or Tyr.

13. The compound of clim 10, said compound selected from the group consisting of:
Clavanin A consisting of amino acid residues
  Val Phe Gln Phe Leu Gly Lys Ile Ile His His Val Gly Asn Phe Val His Gly Phe Ser His Val Phe (SEQ ID NO:39);
Clavanin B consisting of amino acid residues
  Val Phe Gln Phe Leu Gly Arg Ile Ile His His Val Gly Asn Phe Val His Gly Phe Ser His Val Phe (SEQ ID NO:40);
Clavanin C consisting of amino acid residues
  Val Phe His Leu Leu Gly Lys Ile Ile His His Val Gly Asn Phe Val Tyr Gly Phe Ser His Val Phe (SEQ ID NO:41), wherein Tyr may be o-methylated;
Clavanin D consisting of amino acid residues
  Ala Phe Lys Leu Leu Gly Arg Ile Ile His His Val Gly Asn Phe Val Tyr Gly Phe Ser His Val Phe (SEQ ID NO: 42), wherein Tyr may be o-methylated;
Clavanin E consisting of amino acid residues
  Leu Phe Lys Leu Leu Gly Lys Ile Ile His His Val Gly Asn Phe Val His Gly Phe Ser His Val Phe (SEQ ID NO:43);
Clavanin A (3-23) consisting of amino acid residues
  Gln Phe Leu Gly Lys Ile Ile His His Val Gly Asn Phe Val His Gly Phe Ser His Val Phe (SEQ ID NO:47);
Clavanin B (3-23) consisting of amino acid residues
  Gln Phe Leu Gly Arg Ile Ile His His Val Gly Asn Phe Val His Gly Phe Ser His Val Phe (SEQ ID NO:48);
Clavanin C (3-23) consisting of amino acid residues
  His Leu Leu Gly Lys Ile Ile His His Val Gly Asn Phe Val Tyr Gly Phe Ser His Val Phe (SEQ ID NO:49), wherein Tyr may be o-methylated;
Clavanin D (3-23) consisting of amino acid residues
  Lys Leu Leu Gly Arg Ile Ile His His Val Gly Asn Phe Val Tyr Gly Phe Ser His Val Phe (SEQ ID NO: 50), wherein Tyr may be o-methylated;
Clavanin E (3-23) consisting of amino acid residues
  Lys Leu Leu Gly Lys Ile Ile His His Val Gly Asn Phe Val His Gly Phe Ser His Val Phe (SEQ ID NO:51);
Clavanin E (2-23) consisting of amino acid residues
  Phe Lys Leu Leu Gly Lys Ile Ile His His Val Gly Asn Phe Val His Gly Phe Ser His Val Phe (SEQ ID NO:52);
and the amidated forms thereof.

14. A pharmaceutical composition for antimicrobial use which comprises the compound of claim 1 or 10 in admixture with at least one pharmaceutically acceptable excipient.

15. A composition for application to plants or plant environments for conferring resistance to fungal, bacterial or viral infection in plants which comprises the compound of claim 1 or 10 in admixture with at least one environmentally acceptable diluent.

16. A method to prevent the growth of a virus or bacterium or fungus which method comprises contacting a material which supports the growth of said virus or bacterium or fungus with an amount of the compound of claim 1 or 10 effective to prevent said growth, or with a composition containing the compound of claim 1 or 10 as active ingredient.

* * * * *